US009827138B2

(12) United States Patent
Hultgren

(10) Patent No.: US 9,827,138 B2
(45) Date of Patent: Nov. 28, 2017

(54) FABRICATION OF MAXILLOFACIAL SPLINTS

(71) Applicant: Bruce W. Hultgren, Victoria, MN (US)

(72) Inventor: Bruce W. Hultgren, Victoria, MN (US)

( * ) Notice: Subject to any disclaimer, the term of this patent is extended or adjusted under 35 U.S.C. 154(b) by 39 days.

(21) Appl. No.: 14/606,690

(22) Filed: Jan. 27, 2015

(65) Prior Publication Data
US 2015/0210014 A1    Jul. 30, 2015

Related U.S. Application Data

(60) Provisional application No. 61/932,054, filed on Jan. 27, 2014.

(51) Int. Cl.
| | | |
|---|---|---|
| *A61C 13/00* | (2006.01) | |
| *A61C 5/00* | (2017.01) | |
| *A61C 7/00* | (2006.01) | |
| *G06T 17/00* | (2006.01) | |
| *A61F 5/56* | (2006.01) | |
| *A61C 7/08* | (2006.01) | |
| *B29C 67/00* | (2017.01) | |
| *G06F 17/50* | (2006.01) | |
| *B33Y 50/02* | (2015.01) | |

(Continued)

(52) U.S. Cl.
CPC ............. *A61F 5/566* (2013.01); *A61C 7/002* (2013.01); *A61C 7/08* (2013.01); *A61C 5/007* (2013.01); *A61C 7/36* (2013.01); *A61C 13/0004* (2013.01); *B29C 67/0088* (2013.01); *B33Y 50/02* (2014.12); *G05B 2219/45167* (2013.01); *G06F 3/0484* (2013.01); *G06F 17/50* (2013.01); *G06T 17/00* (2013.01); *G06T 2210/41* (2013.01); *G06T 2219/2004* (2013.01); *Y10T 29/49567* (2015.01)

(58) Field of Classification Search
None
See application file for complete search history.

(56) References Cited

U.S. PATENT DOCUMENTS

| | | | | |
|---|---|---|---|---|
| 4,519,386 A | * | 5/1985 | Sullivan | ................. A61C 5/007 128/859 |
| 4,872,449 A | * | 10/1989 | Beeuwkes, III | .... A61F 5/05891 433/19 |

(Continued)

OTHER PUBLICATIONS

Wikipedia Stereolithography definition in technology section; pp. 1-5, 2016.*

(Continued)

*Primary Examiner* — Akash Saxena
(74) *Attorney, Agent, or Firm* — Merchant & Gould P.C.

(57) ABSTRACT

A technique for fabricating a surgical splint for use in correcting a dental condition of a patient. The technique involves obtaining a three-dimensional digital model of lower and upper arch dentitions of the patient having the dental condition. Relative positions of the lower and upper arch dentitions are adjusted with respect to each other in the three-dimensional digital model using a computing device. An electronic model of a splint is generated based on the adjusted relative positions of the lower and upper arch dentitions. A splint is then generated in a physical form from the electronic model of the splint.

7 Claims, 21 Drawing Sheets

(51) Int. Cl.
*G06F 3/0484* (2013.01)
*A61C 7/36* (2006.01)

(56) References Cited

U.S. PATENT DOCUMENTS

| | | | | |
|---|---|---|---|---|
| 5,328,362 | A * | 7/1994 | Watson | A61C 7/00 128/861 |
| 6,027,340 | A * | 2/2000 | Chun | A61C 7/36 433/19 |
| 6,227,861 | B1 * | 5/2001 | Cartledge | A61C 5/00 433/18 |
| 7,708,557 | B2 * | 5/2010 | Rubbert | A61C 5/007 433/172 |
| 7,757,693 | B2 * | 7/2010 | Toussaint | A61F 5/566 128/848 |
| 7,835,811 | B2 * | 11/2010 | Schmitt | A61C 1/084 433/68 |
| 8,454,362 | B2 * | 6/2013 | Rubbert | A61C 8/0036 433/172 |
| 9,256,710 | B2 * | 2/2016 | Boltunov | A61C 7/002 |
| 9,308,056 | B2 * | 4/2016 | Hultgren | A61C 13/34 |
| 9,375,297 | B2 * | 6/2016 | Davison | A61C 13/0003 |
| 2002/0150859 | A1 * | 10/2002 | Imgrund | A61C 7/00 433/24 |
| 2003/0065259 | A1 * | 4/2003 | Gateno | A61B 17/6433 600/425 |
| 2005/0136371 | A1 * | 6/2005 | Abolfathi | A61C 7/08 433/24 |
| 2006/0003292 | A1 * | 1/2006 | Lauren | A61C 5/007 433/215 |
| 2006/0078849 | A1 * | 4/2006 | Parks | A61C 5/00 433/215 |
| 2006/0121407 | A1 * | 6/2006 | Dylina | A61C 7/08 433/25 |
| 2006/0172251 | A1 * | 8/2006 | Voudouris | A61C 7/36 433/18 |
| 2006/0275731 | A1 * | 12/2006 | Wen | A61C 7/00 433/24 |
| 2009/0090371 | A1 * | 4/2009 | Toussaint | A61F 5/566 128/848 |
| 2009/0311647 | A1 * | 12/2009 | Fang | A61C 19/045 433/24 |
| 2010/0043805 | A1 * | 2/2010 | Kelly | A61F 5/566 128/848 |
| 2010/0104998 | A1 * | 4/2010 | Farrell | A61F 5/566 433/6 |
| 2010/0203478 | A1 * | 8/2010 | Rubbert | A61C 5/007 433/212.1 |
| 2011/0094522 | A1 * | 4/2011 | Weisflog | A61C 7/36 128/861 |
| 2011/0155144 | A1 * | 6/2011 | Tousssaint | A61F 5/566 128/848 |
| 2012/0028221 | A1 * | 2/2012 | Williams | A61C 5/007 433/215 |
| 2013/0066598 | A1 * | 3/2013 | Fisker | A61C 11/00 703/1 |
| 2013/0310963 | A1 * | 11/2013 | Davison | A61C 13/0003 700/98 |
| 2014/0162233 | A1 * | 6/2014 | Hultgren | A61C 13/34 434/270 |
| 2014/0326253 | A1 * | 11/2014 | Baratier | A61F 5/566 128/848 |
| 2015/0210014 | A1 * | 7/2015 | Hultgren | B29C 67/0088 128/845 |
| 2015/0238289 | A1 * | 8/2015 | Wouters | A61F 5/566 700/98 |
| 2015/0238345 | A1 * | 8/2015 | Decker | A61B 5/055 128/847 |
| 2015/0245890 | A1 * | 9/2015 | Wouters | A63B 71/085 700/98 |

OTHER PUBLICATIONS

Manufacturing splints for orthognathic surgery using a three-dimensional printer; Marc Christian Metzger et al; Oral Surgery, Oral Medicine, Oral Pathology, Oral Radiology, and Endodontology vol. 105, Issue 2, Feb. 2008, pp. e1-e7.*

* cited by examiner

FABRICATION OF MAXILLOFACIAL SPLINTS

CROSS-REFERENCE TO RELATED APPLICATION

This application claims priority to U.S. patent application Ser. No. 61/932,054 filed on Jan. 27, 2014 and titled FABRICATION OF MAXILLOFACIAL SPLINTS, the disclosure of which is hereby incorporated by reference in its entirety.

BACKGROUND

Maxillofacial surgery can be used to correct various deformities in the jaws. For example, maxillofacial surgery can be performed to address Class II overjet or Class III negative overjet. A Class II overjet occurs when the maxilla and upper teeth project further than the mandible and lower teeth. A Class III negative overjet is observable when the mandible and lower teeth project further than the maxilla and upper teeth.

Some maxillofacial surgery requires detaching the mandible. Then, the relative positioning of the maxilla and mandible is repositioned so that the Class II or Class III issue has been corrected. Splints are sometimes employed to maintain the maxilla and mandible at desired positions during the surgical procedure.

Splints are also sometimes used to change the positions of the upper and lower dentitions for non-surgical purposes, including treatment of temporomandibular joint disorder (TMD) or sleep apnea.

SUMMARY

In general terms, this disclosure is directed to the fabrication of maxillofacial surgical splints. In one possible configuration and by non-limiting example, the surgical splints are formed by generating an electronic model of the splint based on an electronic model of the patient's dentition. The splint is then generated in a physical form from the electronic model.

One aspect is a method of fabricating a splint to be placed between a maxilla and a mandible of a person, the method comprising: obtaining a three-dimensional digital model of lower and upper arch dentitions of the person; adjusting the relative position of the lower and upper arch dentitions with respect to each other in the three-dimensional digital model using a computing device; generating an electronic model of the splint based on the adjusted relative positions of the lower and the upper arch dentitions; and generating the splint in a physical form from the electronic model of the splint.

Another aspect is a computer readable storage device storing data instructions thereon, the data instructions being executable by a processing device to cause the processing device to: define an upper and a lower boundary of an electronic model of a splint; define an inner and an outer boundary of the electronic model of the splint; define an impression of an upper dentition into the plane defined by the upper splint boundary, wherein the impression of the upper dentition contains a first gap buffer; define an impression of a lower dentition into the plane defined by the lower splint boundary, wherein the impression of the lower dentition contains a second gap buffer; and store a set of exterior boundaries of the electronic model of the splint in a computer readable storage device.

A further aspect is A splint comprising: a body formed of a polymeric material: an upper surface of the body having an impression of an upper dentition formed therein; and a lower surface of the body opposite the upper surface having an impression of a lower dentition formed therein; wherein the body is formed by a rapid fabrication machine.

DETAILED DESCRIPTION

Figure 1:
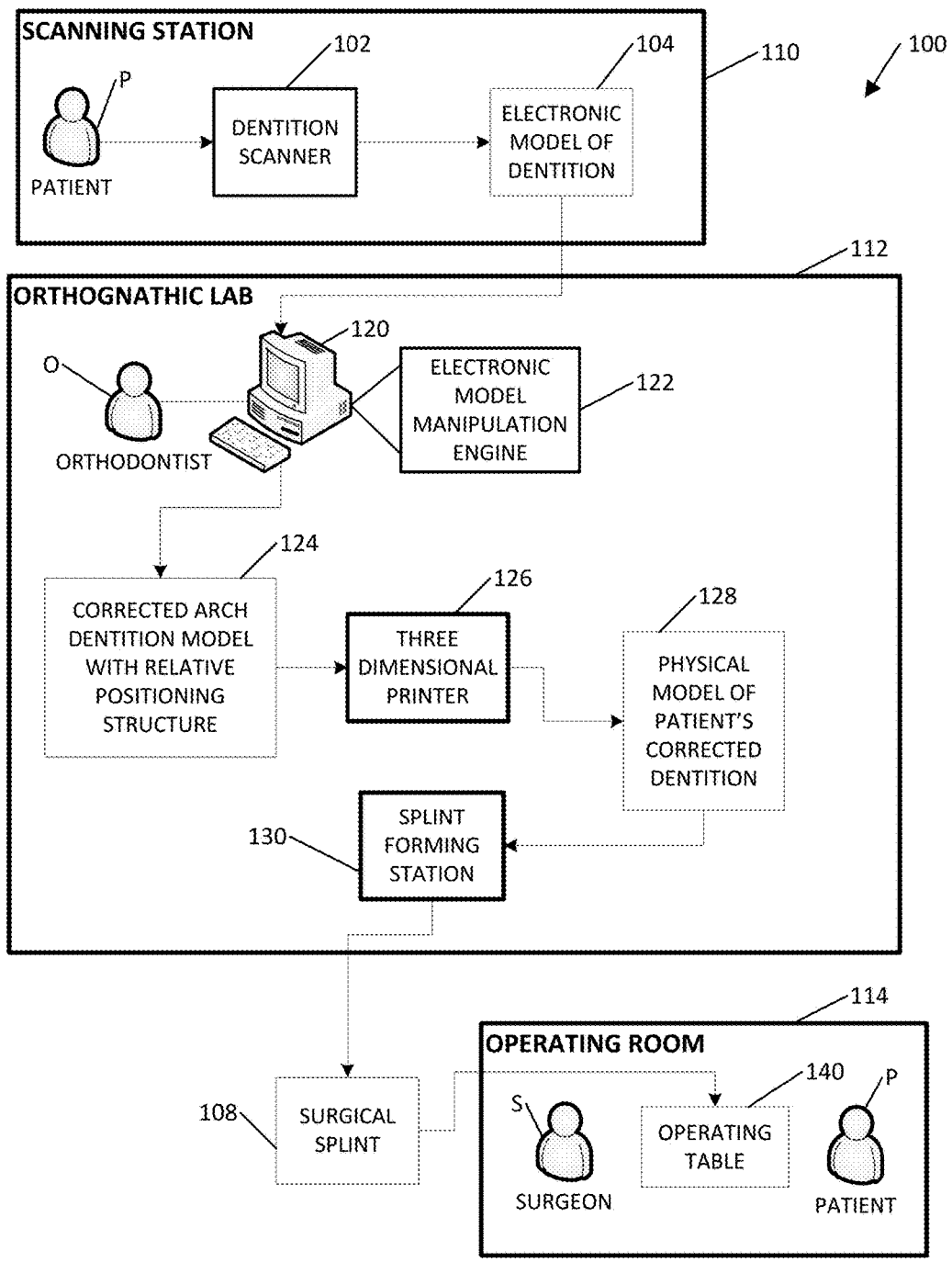
FIG. 1 illustrates a schematic block diagram illustrating an example system for making and using a maxillofacial surgical splint.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 is a schematic block diagram illustrating an example of a system 100 for making and using a maxillofacial surgical splint 108. In this example, the system 100 includes a scanning station 110, an orthognathic lab 112, and an operating room 114. The example scanning station 110 includes a dentition scanner 102 that generates an electronic model 104 of a patient's dentition. The example orthognathic lab 112 includes a computing device 120, an electronic model manipulation engine 122, a corrected arch dentition model 124, a three-dimensional printer 126, a physical model of corrected dentition 128, and a splint forming station 130. The resulting physical splint can be used for orthognathic surgery in an operating room 114, for example, which can include an operating table 140. Also illustrated in FIG. 1 are examples of several people that may be involved with the system 100, including the patient P, orthodontist O, and surgeon S.

The scanning station 110 operates to perform a scan of the patient's P dentition, such as using a dentition scanner 102. In some embodiments, the patient P has been identified as having a dental condition in which the relative positioning of the maxillary and mandibular dentitions needs to be surgically adjusted. Several examples of such dental conditions include, but are not limited to, a Class II overjet or Class III negative overjet, temporomandibular joint disorder (TMD), or sleep apnea.

The scanner 102 operates to perform a scan of the patient's dentition. The scanner 102 can be one of several types, for example, including an intraoral scanner, a table top laser scanner, or a computed tomography (CT) scanner. In some embodiments, the scanner is a three-dimensional laser scanner that generates data defining a polygonal mesh forming the electronic model 104 of the dentition. In some embodiments, the scanner 102 first projects points onto the surface, here, the patient's dentition. The reflection of these points off of the patient's dentition enables the scanner to obtain the location of points in a three-dimensional coordinate system (x, y, z). These points are used to create a point cloud corresponding to the contours of the patient's dentition. Next, the scanning system creates a polygonal mesh by using the point cloud to create triangles that approximate the surface contours. Examples of scanners 102 include a 3D scanner, intraoral scanner, 3D intraoral scanner, or 3D dental scanner. The electronic model may be obtained by placing the scanner in the patient's mouth, by scanning a dental impression, or by scanning from outside of the mouth. Several examples of possible scanners 102 include: the TRIOS Intra Oral Digital Scanner, the Lava Chairside Oral Scanner C.O.S., the iTero, the Cerec AC, the Cyrtina IntraOral Scanner, a cone beam CT (CBCT) scanner, and an industrial CT scanner.

The electronic model 104 of the dentition includes, for example, the maxillary and mandibular dentition, and shows the undesired relative positioning of each that needs to be surgically corrected. Examples of such electronic models 104 are illustrated and described in more detail herein with reference to FIGS. 2 and 3.

The orthognathic lab 112 generates a physical splint 108 for use during the surgical procedure, using the electronic model of dentition 104. The example orthognathic lab 112 includes a computing device 120 including an electronic model manipulation engine 122, a three-dimensional printer 126, and a splint forming station.

The computing device 120 operates to generate a corrected arch dentition model 124 using the electronic model of dentition 104. An example of the computing device 120 is illustrated and described in more detail herein with reference to FIG. 4. In some embodiments, the computing device 120 includes an electronic model manipulation engine 122. The user, such as an orthodontist, interacts with the computing device 120 and electronic model manipulation engine to adjust the relative positioning of the maxillary and mandibular dentitions, and to insert a relative positioning structure, as discussed in more detail herein, to form a corrected arch dentition model 124. An arch dentition includes the dentition, gingiva, and contour of a patient's upper or lower jaw. An example of the electronic model manipulation engine 122 is illustrated and described in more detail herein with reference to FIGS. 5-6.

Figure 16:
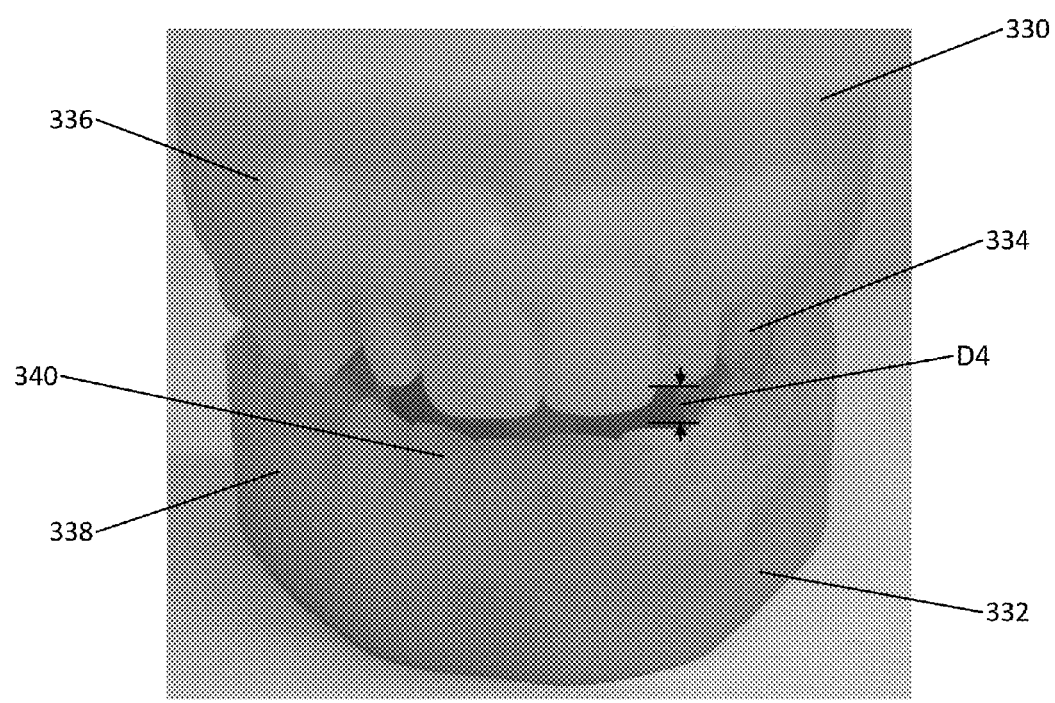
FIG. 16 illustrates a front perspective view of an example physical model of a patient's corrected dentition.
Figure 17:
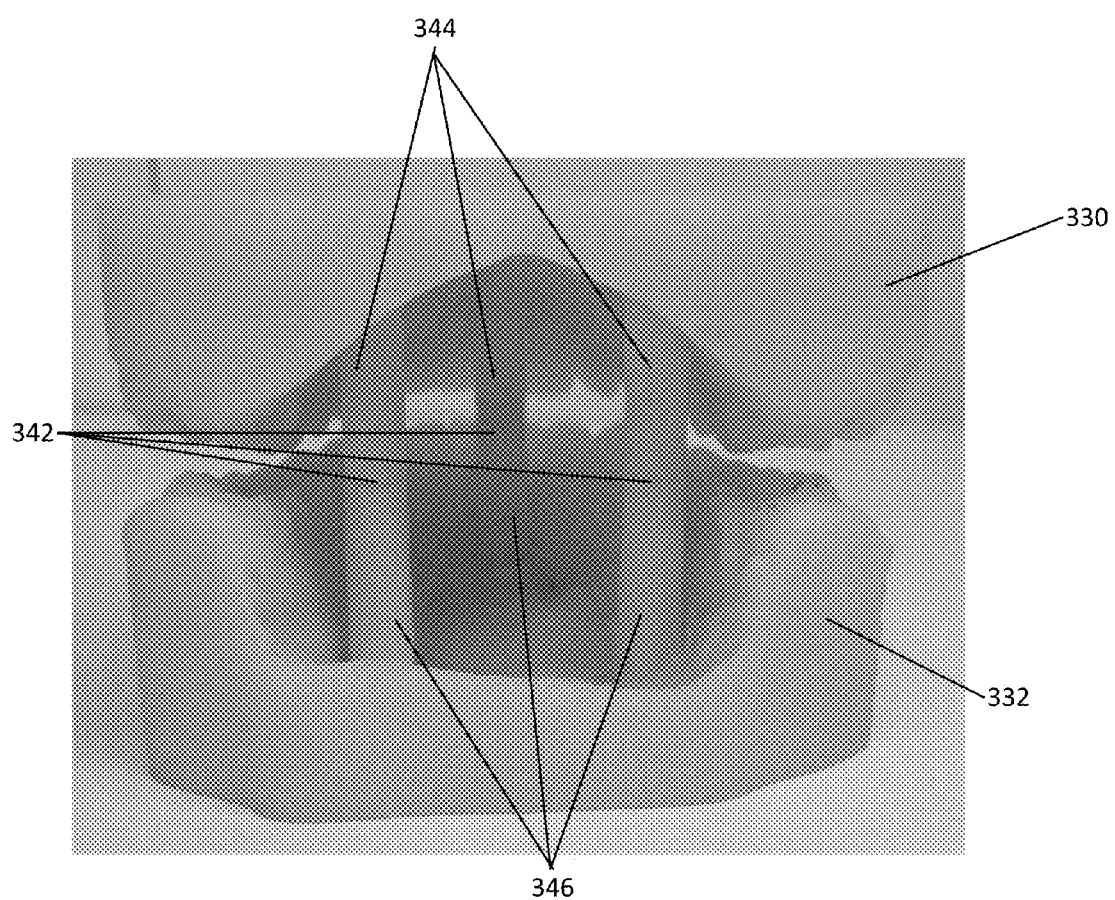
FIG. 17 illustrates a rear perspective view of the example physical model of a patient's corrected dentition with relative positioning structures.

The three-dimensional printer 126 operates to generate a physical model 128 from the corrected arch dentition model 124. In some embodiments, the three-dimensional printer 126 uses an additive process of depositing successive layers of material onto a surface to manufacture a desired object. Electronic three-dimensional models provide the blueprint for the three-dimensional printer: software takes the object within the electronic model and creates thin, horizontal cross-sections which can be used to direct the printer to deposit material at locations defined by the electronic model. Examples of additive technologies include selective laser sintering, fused deposition modeling, stereo lithography, powder bed and inkjet head 3D printing, and plaster-based 3D printing. An example of a three-dimensional printer 126 is the ProJect line of 3D printers available from 3DSystems, Inc. of Rock Hill, S.C. Other examples of three-dimensional printers 126 are those available from Stratysis, Inc. of Eden Prairie, Minn., and Objet Ltd of Rehovot, Israel. In some embodiments the three-dimensional printer 126 is an inkjet printer that utilizes prints using a polymeric material. In another embodiment, the printer 126 is a stereolithography printer that utilizes a photocurable polymer. Other embodiments use other three-dimensional printers. An example of a physical model 128 created by the three-dimensional printer 126 from the corrected arch dentition model 124 are shown in FIGS. 16 and 17.

The splint forming station 130 uses the physical model 128 to form a physical splint 108 that can be used during a surgical procedure. In some embodiments, production of the surgical splint 108 involves inserting a pliable material, such as a light-curable resin, into a space between the upper and lower arch dentitions. In some embodiments, a non-stick coating is first applied to the upper and lower arch dentitions to permit the surgical splint to be more easily separated from the physical model. The pliable material contacts at least some of the teeth of the physical model and is therefore formed with imprints from the teeth that substantially match the shape of the patient's actual teeth. In some embodiments, the material is then cured by illuminating with an ultraviolet light, which hardens the material and decreases its pliability. One example of a suitable material that can be used to form the splint 108 is the TRIAD® transparent VLC custom tray material available from Dentsply International Inc., of York, Pa. In some embodiments, the material is a filled photocure dimethacrylate that polymerizes through exposure to 400- to 500-nm wavelengths ultraviolet-A light.

In some embodiments, the splint material has a paste consistency which can be applied by hand onto the physical model 128. A non-stick material can be applied to the physical model 128 prior to application of the splint material to assist in removal of the splint after it has been formed. The splint material is then placed onto the teeth of one of the upper or lower dentitions 162 and 164, and then the other dentition 162 or 164 is properly positioned using the relative positioning structures, causing the dentitions 162 and 164 to form imprints in the splint material. The splint material can then be hardened by exposing to UV light. The completed splint 108 is then removed from the physical model 128 and is ready for use. In some embodiments, the splint 108 is sterilized prior to use in a surgical environment of the operating room 114.

The surgical splint 108 is formed by the splint forming station, and can be used in some embodiments during a surgical procedure in the operating room 114 to assist in proper positioning of the patient's P maxillary and mandibular dentitions. An example of the surgical splint 108 is illustrated and described in more detail with reference to FIGS. 17-20. In other embodiments, the splint is a non-surgical splint that can be used, for example, to treat TMD or sleep apnea.

In some embodiments, the surgical procedure is performed by a surgeon S in an operating room 114. The patient P can be supported on an operating table 140 or chair during the procedure. During an exemplary procedure, the patient's mandible is broken or cut to permit movement of the mandible. The surgical splint 108 is placed into the patient's mouth, and the maxillary and mandibular dentitions are properly aligned and positioned by locating the teeth in indentations in the surgical splint 108. The mandible is then reconnected to maintain the proper position of the mandible.

Figure 2:
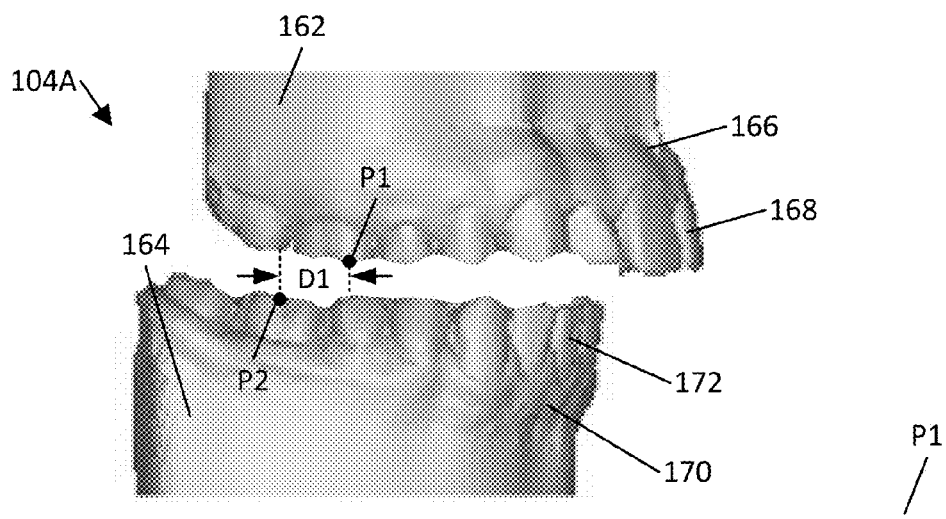
FIG. 2 illustrates a side view of an example three-dimensional electronic model of dentition.

FIG. 2 illustrates an example of a side view of a three-dimensional electronic model of dentition 104, generated by the scanner 102, shown in FIG. 1. The illustrated electronic model 104A shows an example in which the patient has a Class II overjet, which can be identified by the relative positioning of the upper arch dentition 162 and the lower arch dentition 164. A Class II overjet can also be identified, for example, by the distance D1 between corresponding points on the upper dentition 162 and the lower dentition 164, where the upper dentition 162 extends forward farther than the lower dentition 164.

In some embodiments, overjet is identified by reference to particular points on the upper and lower dentitions 162 and 164. An example of such points include the points P1 and P2. Point P1 is the location of the most anterior cusp of the first molar on the upper dentition 162. Point P2 is the location between the anterior and posterior cusps of the lower first molar. In this example, it can be seen that there is a relatively large spacing between points P1 and P2, represented by distance D1, and the point P1 is forward of the point P2. Similarly, corresponding points on the other sides of the dentitions P1 and P2 can be evaluated. Finally, the alignment of the central incisors can be compared from the upper and lower dentitions 162 and 164, as it is typically preferred that the central incisors be aligned on the upper and lower dentitions 162 and 164.

The electronic model 104A of the upper arch dentition 162 defines the contours of the maxillary gingiva 166 and the maxillary teeth 168. Similarly, the electronic model 104A of the lower arch dentition 164 defines the contours of the mandibular gingiva 170 and the mandibular teeth 172. An example of a corrected relative positioning of the upper 162 and lower 164 dentitions is shown in more detail in FIG. 7.

Figure 3:
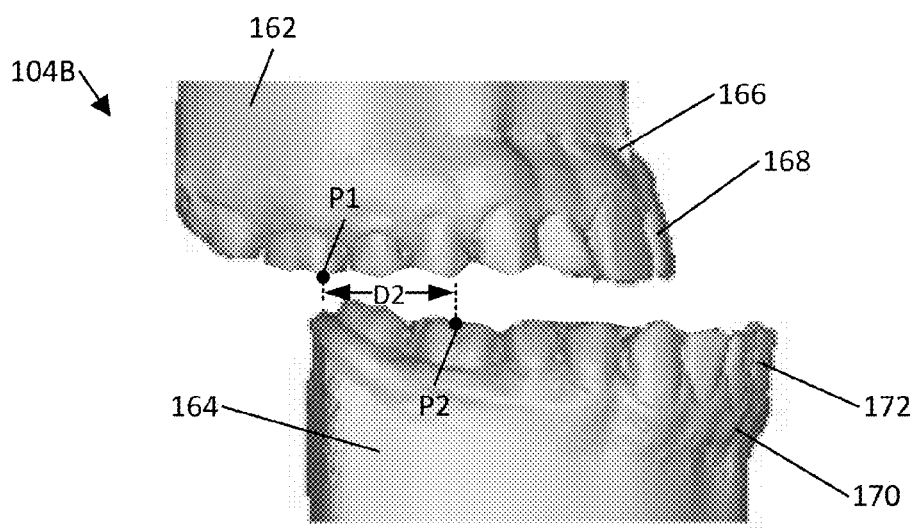
FIG. 3 illustrates a side view of an example three-dimensional electronic model of a patient's dentition.

FIG. 3 illustrates an example of a side view of a three-dimensional electronic model 104 of a patient's dentition, generated by the scanner 102, shown in FIG. 1. The illustrated electronic model 104B shows an example of a Class III negative overjet, which can be identified by the relative positioning of the upper arch dentition 162 and the lower arch dentition 164. A Class II overjet can also be identified, for example, by the distance D2 between two or more corresponding points on the upper dentition 162 and the lower dentition 164, where the lower dentition 164 extends forward farther than the upper dentition 162.

In some embodiments, negative overjet is identified by reference to particular points on the upper and lower dentitions 162 and 164. An example of such points include the points P1 and P2, as discussed above. Point P1 is the location of the most anterior cusp of the first molar on the upper dentition 162. Point P2 is the location between the anterior and posterior cusps of the lower first molar. In this example, it can be seen that there is a relatively large spacing between points P1 and P2, represented by distance D2, and the point P2 is forward of the point P1.

The electronic model 104B of the upper arch dentition 162 defines the contours of the maxillary gingiva 166 and the maxillary teeth 168. Similarly, the electronic model 104A of the lower arch dentition 164 defines the contours of the mandibular gingiva 170 and the mandibular teeth 172. An example of a corrected relative positioning of the upper 162 and lower 164 dentitions is shown in more detail in FIG. 7.

Figure 4:
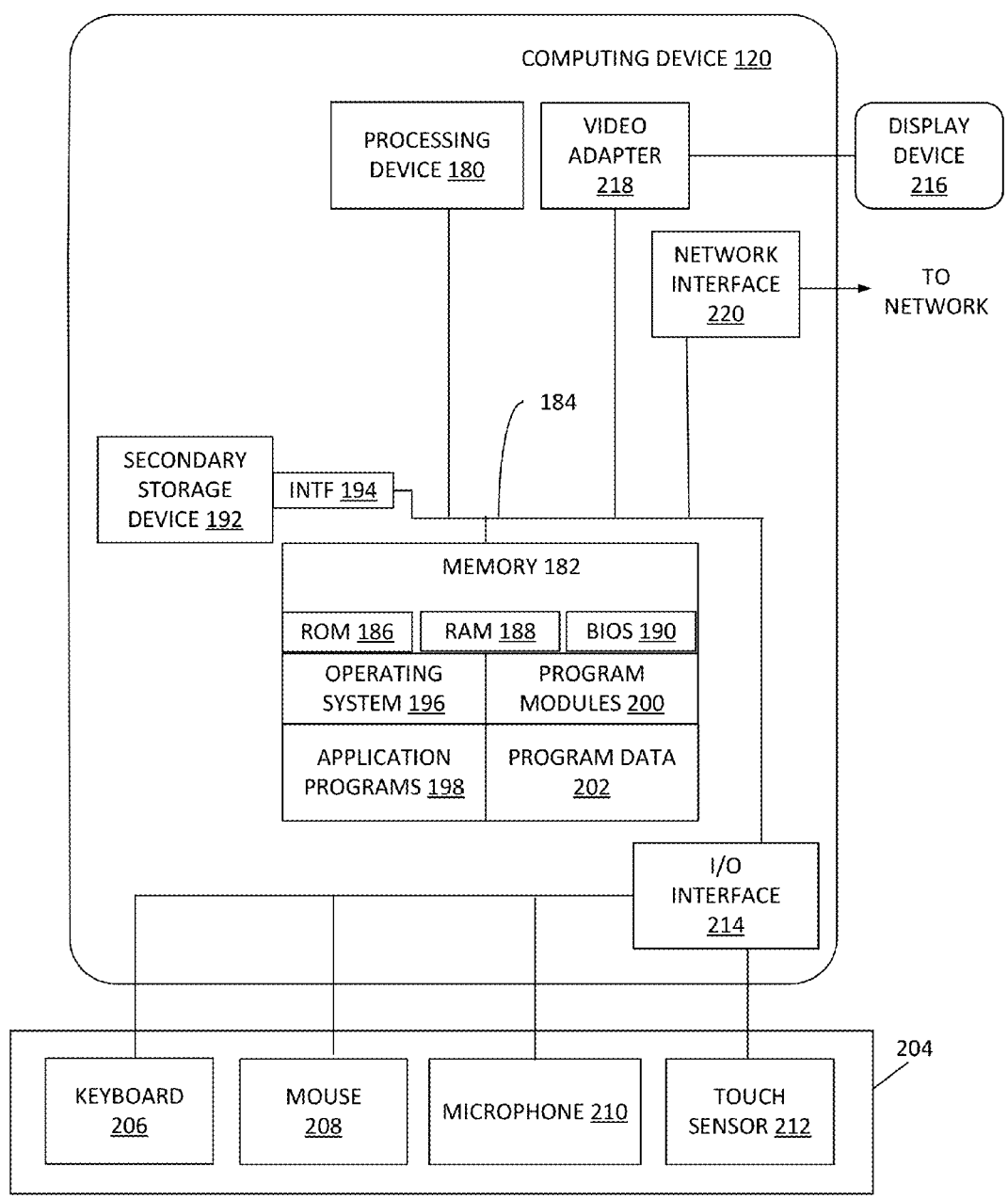
FIG. 4 illustrates an example architecture of a computing device, which can be used to implement aspects according to the present disclosure.

FIG. 4 illustrates an exemplary architecture of a computing device that can be used to implement aspects of the present disclosure, including any of the plurality of computing devices described herein, such as a computing device of the dentition scanner 102, the electronic model manipulation engine 122, a computing device of the three dimensional printer 126, or any other computing devices that may be utilized in the various possible embodiments. The computing device illustrated in FIG. 4 can be used to execute the operating system, application programs, and software modules (including the software engines) described herein. By way of example, the computing device will be described below as the computing device 120 that operates the electronic model manipulation engine 122. To avoid undue repetition, this description of the computing device will not be separately repeated herein for each of the other possible computing devices, but such devices can also be configured as illustrated and described with reference to FIG. 4.

The computing device 120 includes, in some embodiments, at least one processing device 180, such as a central processing unit (CPU). A variety of processing devices are available from a variety of manufacturers, for example, Intel or Advanced Micro Devices. In this example, the computing device 120 also includes a system memory 182, and a system bus 184 that couples various system components including the system memory 182 to the processing device 180. The system bus 184 is one of any number of types of bus structures including a memory bus, or memory controller; a peripheral bus; and a local bus using any of a variety of bus architectures.

Examples of computing devices suitable for the computing device 120 include a desktop computer, a laptop computer, a tablet computer, a mobile computing device (such as a smart phone, an iPod® or iPad® mobile digital device, or other mobile devices), or other devices configured to process digital instructions.

The system memory 182 includes read only memory 186 and random access memory 188. A basic input/output system 190 containing the basic routines that act to transfer information within computing device 120, such as during start up, is typically stored in the read only memory 186.

The computing device 120 also includes a secondary storage device 192 in some embodiments, such as a hard disk drive, for storing digital data. The secondary storage device 192 is connected to the system bus 184 by a secondary storage interface 194. The secondary storage devices 192 and their associated computer readable media provide nonvolatile storage of computer readable instructions (including application programs and program modules), data structures, and other data for the computing device 120.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media. Additionally, such computer readable storage media can include local storage or cloud-based storage.

A number of program modules can be stored in secondary storage device 192 or memory 182, including an operating system 196, one or more application programs 198, other program modules 200 (such as the software engines described herein), and program data 202. The computing device 120 can utilize any suitable operating system, such as Microsoft Windows™, Google Chrome™, Apple OS, and any other operating system suitable for a computing device. Other examples can include Microsoft, Google, or Apple operating systems, or any other suitable operating system used in tablet computing devices.

In some embodiments, a user provides inputs to the computing device 120 through one or more input devices 204. Examples of input devices 204 include a keyboard 206, mouse 208, microphone 210, and touch sensor 212 (such as a touchpad or touch sensitive display). Other embodiments include other input devices 204. The input devices are often connected to the processing device 180 through an input/output interface 214 that is coupled to the system bus 184. These input devices 204 can be connected by any number of input/output interfaces, such as a parallel port, serial port, game port, or a universal serial bus. Wireless communication between input devices and the interface 214 is possible as well, and includes infrared, BLUETOOTH® wireless technology, 802.11a/b/g/n, cellular, or other radio frequency communication systems in some possible embodiments.

In this example embodiment, a display device 216, such as a monitor, liquid crystal display device, projector, or touch sensitive display device, is also connected to the system bus 184 via an interface, such as a video adapter 218. In addition to the display device 216, the computing device 120 can include various other peripheral devices (not shown), such as speakers or a printer.

When used in a local area networking environment or a wide area networking environment (such as the Internet), the computing device 120 is typically connected to the network through a network interface 220, such as an Ethernet interface. Other possible embodiments use other communication devices. For example, some embodiments of the computing device 120 include a modem for communicating across the network.

The computing device 120 typically includes at least some form of computer readable media. Computer readable media includes any available media that can be accessed by the computing device 120. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 120.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device illustrated in FIG. 4 is also an example of programmable electronics, which may include one or more such computing devices, and when multiple computing devices are included, such computing devices can be coupled together with a suitable data communication network so as to collectively perform the various functions, methods, or operations disclosed herein.

Figure 5:
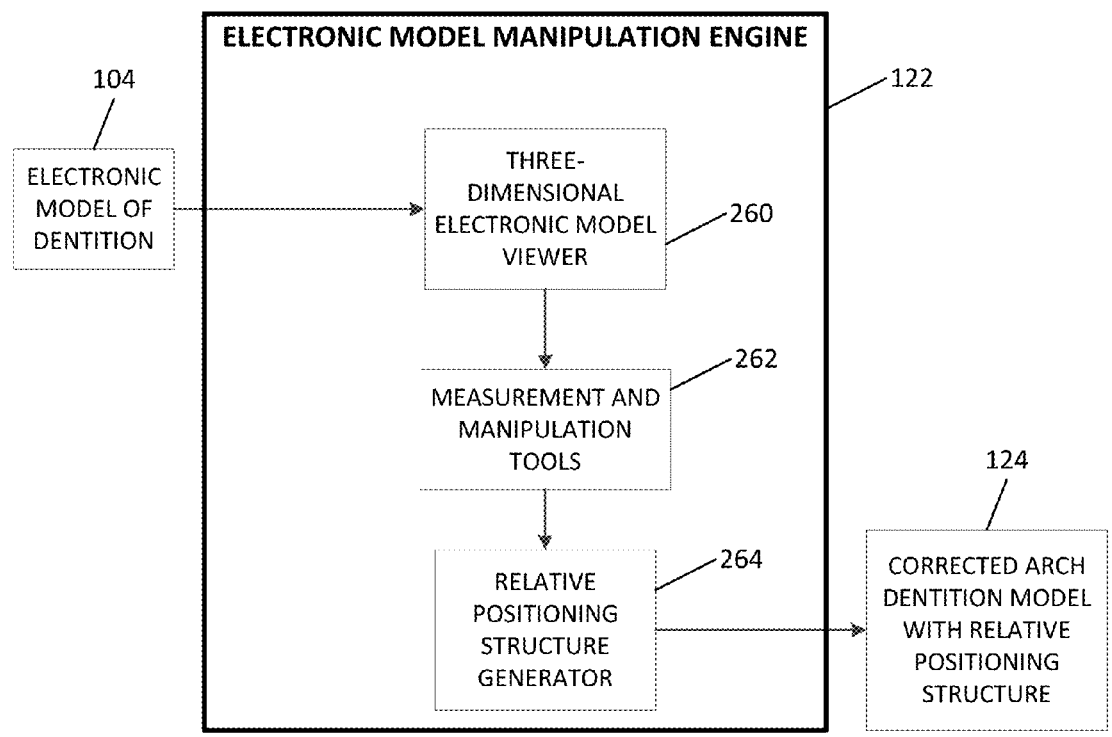
FIG. 5 illustrates a schematic block diagram illustrating an example electronic model manipulation engine.

FIG. 5 is a schematic block diagram illustrating an example of an electronic model manipulation engine 122. In this example, the model manipulation engine 122 includes a three-dimensional electronic model viewer 260, measurement and manipulation tools 262, and a relative positioning structure generator 264. Also illustrated in FIG. 5 are the electronic model of dentition 104 and the corrected arch dentition model 124 with relative positioning structure.

The three-dimensional electronic model viewer 260 operates to display the electronic model of dentition 104 generated by the dentition scanner 102 to a user, such as the orthodontist O, so that the user can view it. In one embodiment, the electronic model viewer 260 reads the received electronic model 104 data and renders the electronic model 104 viewable in the computing device 120. In some embodiments, the electronic model viewer 260 converts the file type of the received electronic model 104 into another format readable by the computing device 120, prior to displaying the electronic model of dentition 104 to the user O. An example of a three-dimensional electronic model viewer is the EMODEL® Viewer, such as version 8.5, available from GeoDigm Corporation, of Falcon Heights, Minn.

The measurement and manipulation tools 262 enable the user O to reposition the relative alignment of the upper 162 and lower 164 arch models. In one embodiment, the tools 262 render the upper 162 and lower 164 arch models independently maneuverable. In some embodiments, the user O utilizes the tools 262 to adjust the relative positions of the arch dentitions. The user O can reposition both the upper 162 and lower 164 arch models in any of the x-, y-, or z-planes to correct the diagnosed condition. In another embodiment, the tools 262 measure the relative positions of two or more corresponding points on the upper 162 and lower 164 arch models to obtain a distance D3. In this embodiment, the tools 262 are programmed to automatically compare the new distance D3 with a pre-defined metric automatically positioning the upper 162 and lower 164 arch models according to the pre-defined metric. Alternatively, the tools 262 can be used to instruct the user to continue repositioning the upper 162 and/or lower 164 arch models if the current relative positioning does not satisfy the metrics. In some embodiments, the measurement and manipulation tools 262 are part of the Modified Bite Module of the EMODEL® Viewer software application. For example, manipulation of the electronic model can be accomplished using the rotate x-y-z and translate x-y-z functions. Measurement can be accomplished, for example, using the measurement grid function. In another possible embodiment, the measurement and manipulation tools 262 can be configured to automatically configure the upper and lower dentitions 162 and 164 according to predefined criteria, or by user-provided criteria, such as desired measurements between particular points (e.g., P1 and P2 discussed herein, and the alignment of the central incisors).

In some embodiments, the tools 262 include a measurement tool for measuring the distance between at least two points of the upper and lower arch dentitions 162 and 164. An example showing the measurement of distance D4 after the repositioning of the upper 162 and lower 164 arch dentitions, is illustrated and described in more detail with reference to FIG. 7.

The relative positioning structure generator 264 operates to add to the electronic model 104 structures that will hold and maintain the relative positioning of the upper and lower arch dentitions 162 and 164, after the position of such arch dentitions 162 and 164 has been corrected in the electronic model 104. The relative positioning structure generator is illustrated and described in more detail with reference to FIG. 6.

Figure 6:
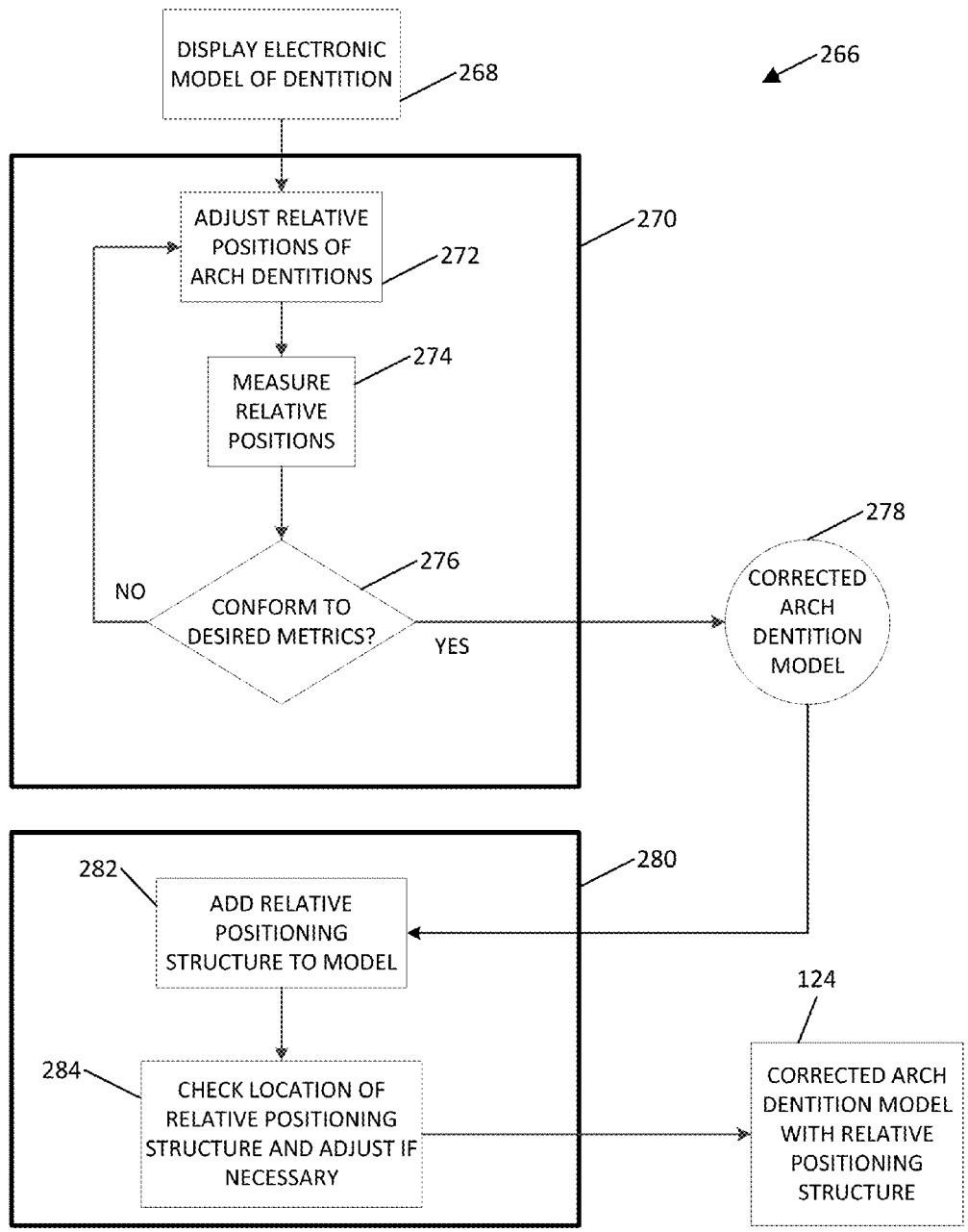
FIG. 6 illustrates a flow chart showing an example method of correcting improper alignment of the maxilla and the mandible.

FIG. 6 is a flow chart illustrating an example method 266 of correcting an improper alignment of the maxilla and the mandible. In this example, the method 266 includes operation 268 and methods 270 and 280. The method 266 transforms an electronic model of improperly aligned maxilla and mandible into a corrected model where the maxilla and mandible are properly aligned and the model has one or more relative positioning structures.

Operation 268 is performed to enable the user to view the electronic model of dentition 104. In some embodiments, operation 268 is performed by the three-dimensional electronic model viewer 260, shown in FIG. 5.

In this example, the method 270 is performed to adjust the relative positioning of the upper 162 and lower 164 dentition models, where the corrected relative positions are illustrated and described in more detail with reference to FIG. 7. The method includes operations 272, 274, and 276. In some embodiments, the method 270 is performed by the three-dimensional electronic model viewer 260 and the measurement and manipulation tools 262, shown in FIG. 5.

Operation 272 is performed to adjust the relative positions of the upper 162 and lower 164 arch dentitions. In some embodiments, the operation 272 interacts with the user to manipulate the relative positions of the arch dentitions 162 and 164. Based on the patient's condition, the operation 272 prompts the user O to reposition the patient's maxilla and mandible in the x-y plane, and receives inputs from the user to make the appropriate adjustments.

Operation 274 is performed to measure the relative positions of the upper 162 and lower 164 arch dentitions. In some embodiments, the operation 274 identifies two corresponding points on the upper 162 and lower 164 arch dentitions. As an example, the operation 274 calculates the distance, see D3 in FIG. 7, in the x-y-plane between two lines that pass through the identified points, where the lines are normal to the x-y-plane. For example, the operation 274 may select points on the labial surface of the maxillary and mandibular central incisors. In other embodiments, the operation 274 calculates the vertical distance between two corresponding points, see D4 in FIG. 7, on the upper 168 and lower 172 dentitions. For example, the operation 274 may select points on the occlusal surface of the $2^{nd}$ molars and calculate the vertical or z-plane distance between those points.

Operation 276 is performed to verify that the relative positioning of the upper 162 and lower 164 arch dentitions conforms to desired metrics. In some embodiments, pre-defined parameters are stored. An example of pre-defined parameters are metrics related to the required relative horizontal (x-y plane) positions of the upper 162 and lower 164 arch dentitions needed to correct the observed deficiency. Another example of pre-defined parameters are metrics corresponding to the manufacturing characteristics of the splint forming station 130. These parameters measure the z-plane or vertical distance between the upper 168 and lower 172 dentition.

In some embodiments, the operation 276 compares the relative position of the upper 162 and lower 164 arch dentitions. As an example, if the positions do not correspond to the desired metrics, the operation 276 prompts the user to readjust the relative positions in operation 272 and the process repeats until the arch dentitions are acceptably positioned. In one embodiment, if the relative positions do not conform to the pre-stored metrics, the operation 276 reposition the upper 162 and lower 164 arch dentitions so that the relative positions satisfy the metric criteria. As another example, if the positions are within acceptable tolerances of the pre-stored metrics, the operation 276 prompts the user to complete the model with operations 280 and 282. An example of a corrected arch dentition model 278 is illustrated and described in more detail with reference to FIG. 7.

In this example, the method 280 is performed to add relative positioning structures to the model. The method includes operations 282 and 284. In some embodiments, the method 280 is performed by the three-dimensional electronic model viewer 260 and the relative positioning structure generator 264, shown in FIG. 5. In some embodiments, the method 280 begins when the engine accesses the corrected arch dentition model 278. In some embodiments, the method 280 may be performed by a user who is not the orthodontist O.

Operation 282 is performed to add one or more relative positioning structures to the arch dentition model 278. In some embodiments, the operation 282 prompts the user to select a type of relative positioning structure from a database containing templates for different relative positioning structures.

In one embodiment, the operation 282 prompts the user to select a position for the relative positioning structure on the lower arch dentition 164, and the operation 282 receives the input from the user. In some embodiments, the operation 282 continues to prompt the user to select positions of additional relative positioning structures. Alternatively, the operation 282 prompts the user to select a position for the upper arch dentition 162 first; the order is not important. In some embodiments, the operation 282 adds one or more complementary relative positioning structures to the opposite dentition. In one embodiment, the operation 282 creates the relative positioning structures by accessing the templates defining the properties of the relative positioning structures.

FIGS. 8-15 illustrate an example of relative positioning structures as having cylindrical bases with male and female couplings, where the male coupling is in the shape of a truncated cone. This is only an example. In other possible embodiments, other shapes, configurations, and quantities of relative positioning structures can be used. Some examples include where the relative positioning structure is between or located on outside the upper and lower arch dentition. For example, a single structure that simultaneously holds the upper 162 and lower 164 arch dentitions, which is between the arch dentitions, or a c-shaped structure that holds the two arch dentitions without passing between the arch dentitions. In other embodiments, the relative positioning structure is a single structure, in contrast to the three structures shown in more detail in FIGS. 8-11, where the body has a larger surface area than the structures shown in FIGS. 8-11. In yet other embodiments, the relative positioning structure is two or more structures. In some embodiments, the relative positioning structures have bodies in other polyhedron shapes, such as triangular or rectangular prisms, in contrast to the cylindrical bodies shown in more detail in FIGS. 8-11. An example of the relative positioning structure is illustrated and described with reference to FIGS. 8-11.

Operation 284 is performed in some embodiments to ensure that the relative positioning structure or structures do not interfere with the subsequent surgical splint formation. In some embodiments, the operation 284 prompts the user to check the location of the relative positioning structure created by the operation 284 on the opposite dentition. In other embodiments, the operation 284 notifies the user that the current position of the relative positioning structure could interfere with the production of the surgical splint. As an example, the operation 284 accesses a database containing the various space requirements for different surgical splint production methods. Examples of such requirements could be the predicted width, in the x-y-plane, of surgical splints formed using different materials.

In some embodiments, the operation 284 receives the user's selection of new positions for the relative positioning structures. As an example, after receiving the user's input the operation 284 updates the position of the complementary positioning structure. In one embodiment, the operation 284 repeats until the relative positioning structure or structures do not potentially interfere with the surgical splint production. In other embodiments, once the operation 284 has received the user's input selecting relative positioning structures, the model 124 is ready for the three-dimensional printer 126.

Figure 7:
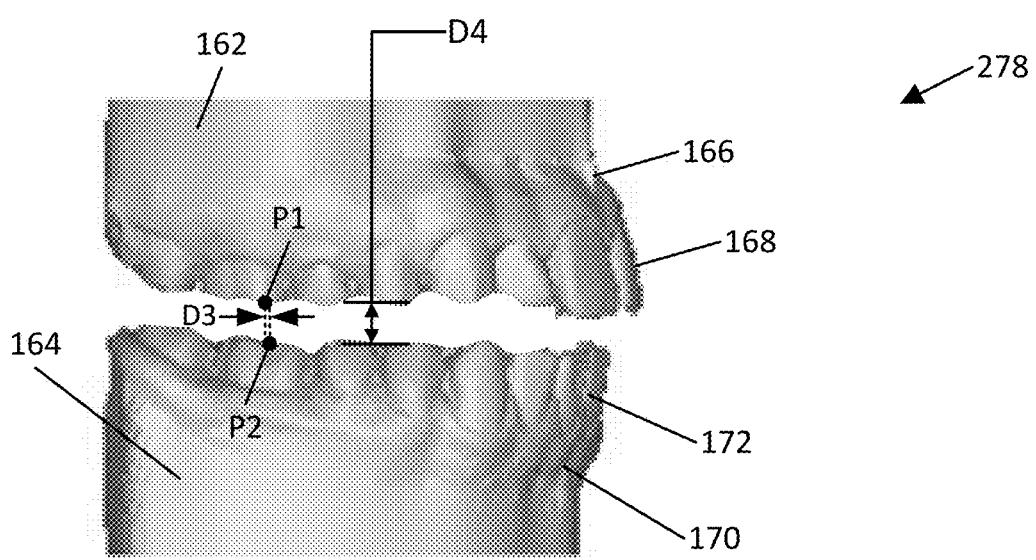
FIG. 7 illustrates a side view of an example three-dimensional electronic model with corrected positioning of the maxilla and mandible.

FIG. 7 illustrates a side view of an example of a corrected arch dentition model 278, such as generated by the method 270 shown in FIG. 6. In this example, the model 278 includes the upper 162 and lower 164 arch dentitions, the maxillary 166 and mandibular 170 gingiva, and the upper 168 and lower 172 dentition. In this example, upper 162 and lower 164 arch dentitions are positioned to correct the diagnosed condition of the patient P.

In some embodiments, the horizontal distance D3 is the distance in the x-y-plane between corresponding points on the upper 162 and lower 164 arch dentitions. In some embodiments, the two corresponding points are the same points used in measuring and obtaining the horizontal distance D1 or D2, as shown in FIGS. 2 and 3. In some embodiments, the vertical distance D4 is the distance in the x-z- or y-z-plane between two corresponding points on the upper 162 and lower 164 arch dentitions. In some embodiments, the electronic model manipulation engine 122 is used to obtain the model shown in FIG. 7.

Figure 8:
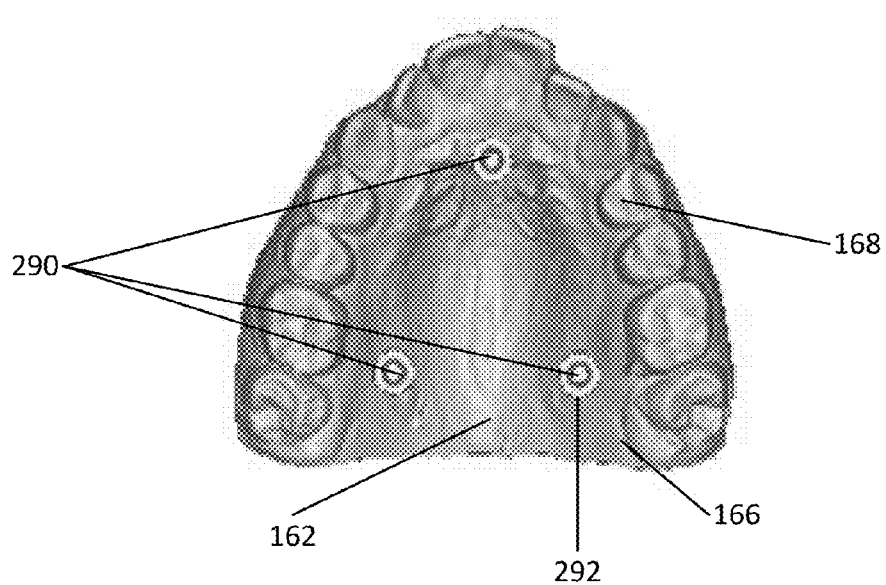
FIG. 8 illustrates a screenshot of the upper arch dentition with relative positioning structures.

FIG. 8 is a screenshot of the upper arch dentition 162 with relative positioning structures 290 as displayed by the electronic model manipulation engine 122, shown in FIG. 5. The screenshot shows the upper arch dentition 162, the upper dentition 168, the maxillary gingiva 166, and the location 292 of the relative positioning structures 290.

The relative positioning structure 290 functions to hold the upper 162 and lower 164 arch dentitions in the adjusted relative positions. In some embodiments, the relative positioning structures 290 in the upper arch dentition 162 have a shape that is complementary to the relative positioning structures 294, shown in FIG. 9, in the lower arch dentition 164. The relative positioning structures 290 are shown and described in more detail in FIGS. 10 and 12.

The location 292 of the relative positioning structures 290 functions to enable the relative positioning structures 290 to hold the physical model 128 in the adjusted positions without interfering with the surgical splint 108 production. In one embodiment, the engine 122 prompts the user to select a position 292 of a relative positioning structure 290, as described in operation 282. As an example, the engine 122 receives the input selecting the position 292, where the position 292 is preferably not in contact with the maxillary gingiva 166 or upper dentition 168. In another embodiment, the engine 122 prompts the user for the position 292 of two more relative positioning structures 290.

Figure 10:
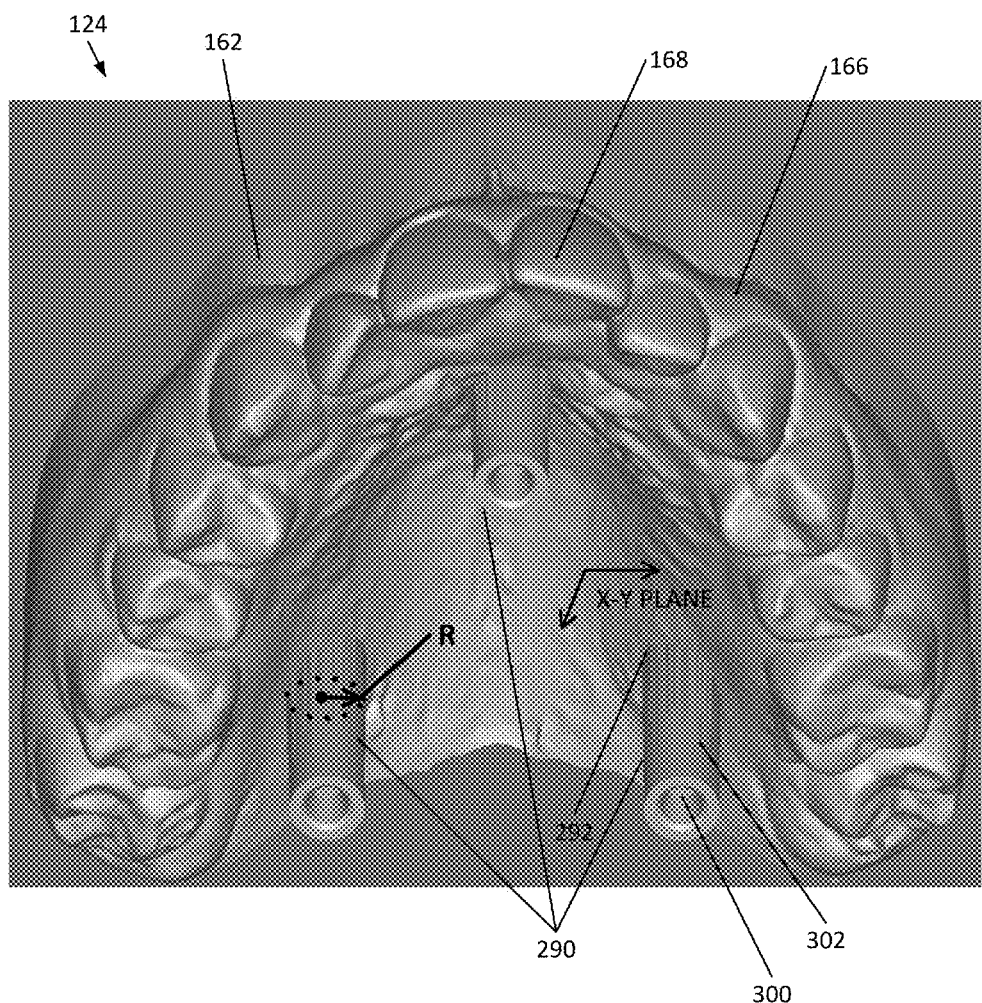
FIG. 10 illustrates a perspective view of an example corrected arch dentition model with relative positioning structures.

In some embodiments, the engine 122 corrects the location 292 of the relative positioning structures 290 so the structures do not interfere with the surgical splint 108 production. As an example, the engine 122 has verified that the location 292 of the relative positioning structures 290 in FIG. 8 do not interfere with the splint 108 production. The location 292 of the relative positioning structures 290 is also illustrated in FIG. 10.

Figure 9:
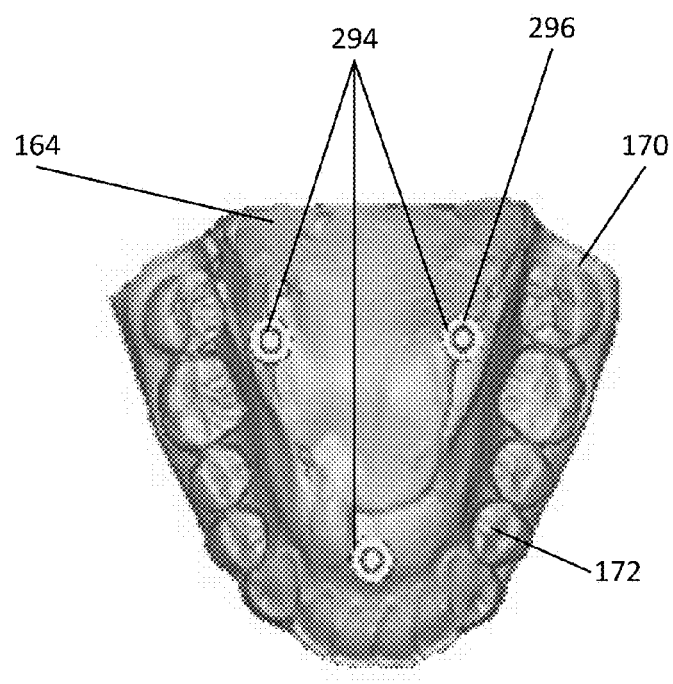
FIG. 9 illustrates a screenshot of the lower arch dentition with relative positioning structures.

FIG. 9 is a screenshot of the lower arch dentition 164 with relative positioning structures 294. The screenshot shows the lower arch dentition 164, the lower dentition 172, the mandibular gingiva 170, and the location 296 of the relative positioning structures 294.

The relative positioning structure 294 functions to hold the upper 162 and lower 164 arch dentitions in the adjusted relative positions 278. In some embodiments, the relative positioning structures 294 in the lower arch dentition 164 have a shape that is complementary to the relative positioning structures 290, shown in FIG. 8, in the upper arch dentition 162. The relative positioning structures 294 are shown and described in more detail in FIGS. 11 and 12.

The location 296 of the relative positioning structures 294 functions to enable the positioning structures 294 to hold the physical model 128 in the adjusted positions without interfering with the surgical splint 108 production. In one embodiment, the engine 122 prompts the user to select a position 296 of a relative positioning structure 294, as described in operation 282. As an example, the engine 122 receives the input selecting the position 296, where the position 296 is preferably not in contact with the mandibular gingiva 170 or lower dentition 172. In another embodiment, the engine 122 prompts the user for the position 296 of two more relative positioning structures 294.

In some embodiments, the engine 122 corrects the location 296 of the relative positioning structures 294 so the structures do not interfere with the surgical splint 108 production. As an example, the engine 122 has verified that the location 296 of the relative positioning structures 294 in FIG. 9 do not interfere with the splint 108 production. The location 296 of the relative positioning structures 294 is also described in FIG. 11.

FIG. 10 illustrates a perspective view of an example corrected arch dentition model 124 with relative positioning structures 290. The illustrated model shows an example of an upper arch dentition 162 in which there are three relative positioning structures 290 with a given radius R. Also illustrated is the location 292 of the structures 290, including an example coupling feature 300 and a body 302. The upper dentition 168 and the maxillary gingiva 166 are also shown.

The location 292 of the relative positioning structures 290 in FIG. 10 functions to stably connect to the lower arch dentition 164 while also not interfering with surgical splint 108 production.

The female coupling 300 on the relative positioning structure 290 receives the male coupling 308 from the opposite arch dentition. In one embodiment, the relative positioning structures 290 and 294 have complementary female 300 and male 308 couplings. In one embodiment, the female coupling 300 has a recessed portion that is sized and shaped to receive the corresponding protruding portion of the male coupling 308 (shown in FIG. 11). In this example, the female coupling 300 is on the relative positioning structures 290 in the upper arch dentition 162, but the engine can place the female coupling 300 on either the upper 162 or the lower 164 arch dentition. An example of a male-female coupling interaction is shown in more detail in FIG. 12.

The body 302 extends between the arch dentition 162 and the coupling 300. In some embodiments, the body 302 protrudes normal to the x-y-plane from the upper arch dentition 162. In one embodiment, the contours of the upper arch dentition 162 flow seamlessly with the body 302 so that the three-dimensional printer 126 produces the upper arch 164 and positioning structures 290 as one continuous piece. In some embodiments, the body 302 of the relative positioning structure 290 is cylindrically shaped. In some embodiments, the engine 122 accesses a template which is used to create the relative positioning structure. As an example, the engine 122 receives the user's point selection of the center of the positioning structure 290 as well as the desired radius R of the cylindrical body 302 extending therefrom. As another example, the engine 122 receives the user's selection of the height of the cylindrical body 302. The bodies and the connected relative positioning structures are shown in more detail in FIGS. 13-15.

Figure 11:
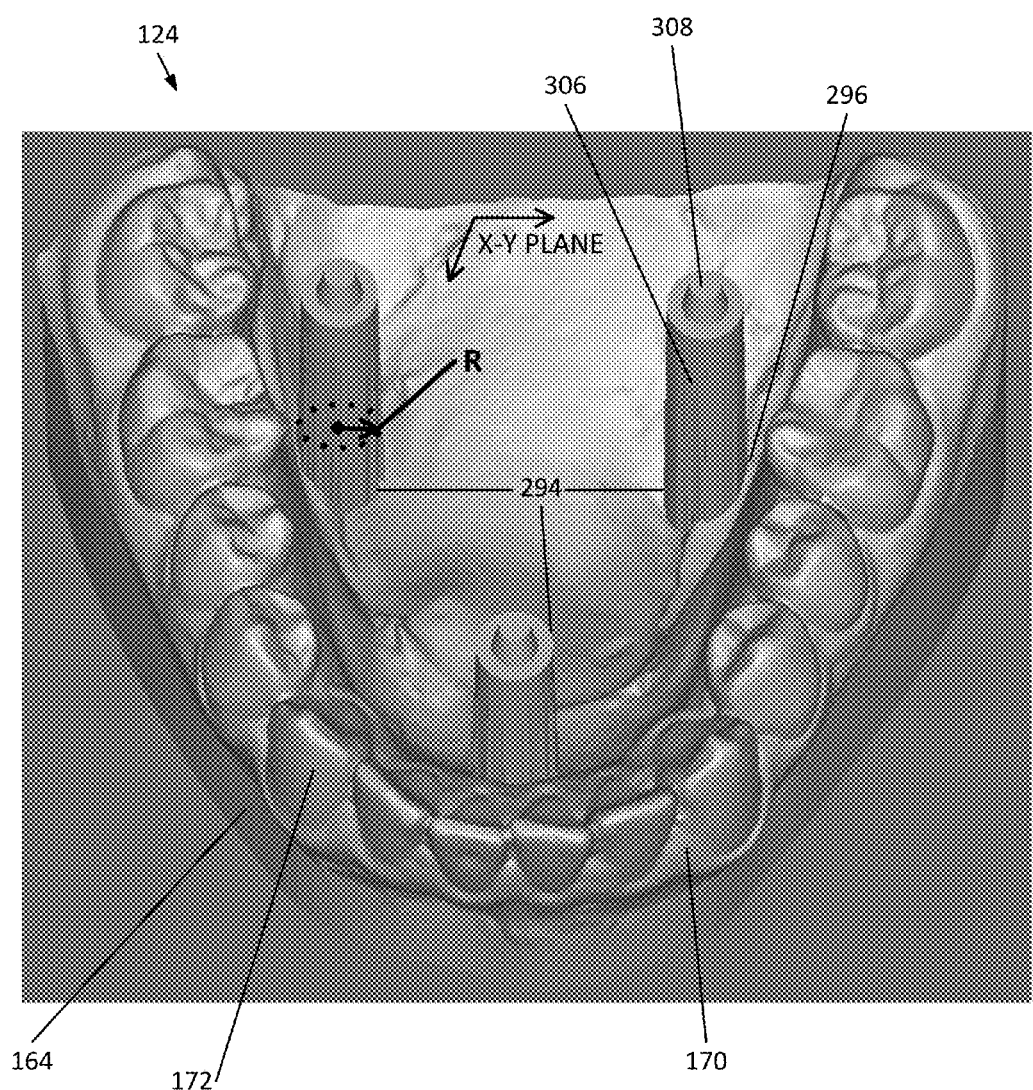
FIG. 11 illustrates another perspective view of the example corrected arch dentition model with relative positioning structures.

FIG. 11 illustrates a perspective view of an example corrected arch dentition model 124 with relative positioning structures 294. The illustrated model shows an example of a lower arch dentition 164 in which there are three relative positioning structures 290 with a given radius R. Also illustrated is the location 296 of the relative positioning structures 294, an example male coupling 308 and support body 306 of a positioning structure, the lower dentition 172, and the mandibular gingiva 170.

The location 296 of the relative positioning structures 294 in FIG. 11 functions to stably connect to the upper arch dentition 162 while also not interfering with surgical splint 108 production.

The male coupling 308 on the relative positioning structure 294 fits into the female coupling 300 of the relative positioning structure 290 of the opposite arch dentition. In one embodiment, the relative positioning structures 290 and 294 have complementary female 300 and male 308 couplings. In one embodiment, the male coupling 308 is a truncated cone. In this example, the male coupling 308 is on the relative positioning structures 294 in the lower arch dentition 164, but the engine can place the male coupling 308 on either the upper 162 or the lower 164 arch dentition. An example of a male-female coupling interaction is shown in more detail in FIG. 12.

The body 306 supports the coupling 308. In some embodiments, the body 306 protrudes normal to the x-y-plane from the lower arch dentition 164. In one embodiment, the contours of the upper arch dentition 162 flow seamlessly with the body 302 so that the three-dimensional printer 126 produces the upper arch 164 and relative positioning structures 290 as one continuous piece. In some embodiments, the body 306 of the relative positioning structure 294 is cylindrically shaped. In some embodiments, the engine 122 accesses a template which is used to create the relative positioning structure. As an example, the engine 122 receives the user's point selection of the center of the positioning structure 296 as well as the desired radius R of the cylindrical body 306 extending therefrom. As another example, the engine 122 receives the user's selection of the height of the cylindrical body 306. The bodies and the connected relative positioning structures are shown in more detail in FIGS. 13-15.

Figure 12:
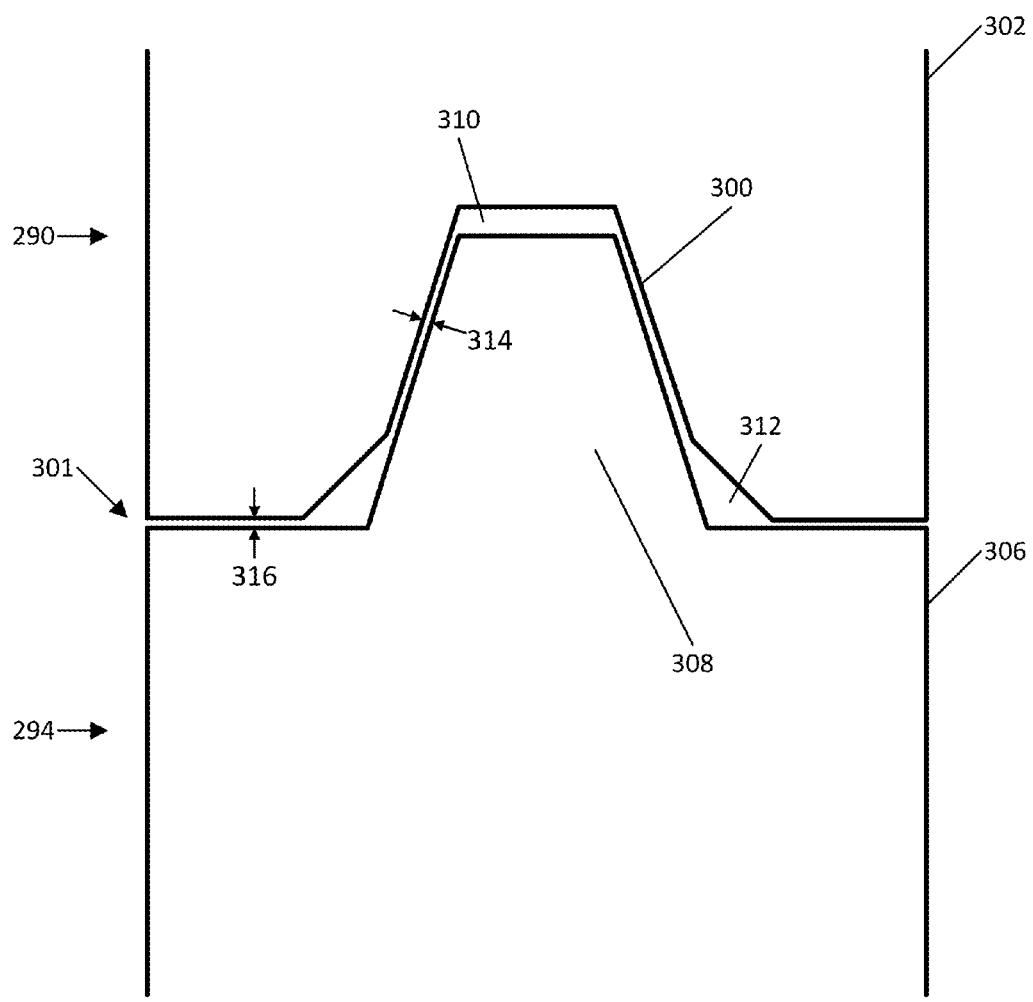
FIG. 12 illustrates a cross sectional view of an example connection between two relative positioning structures.

FIG. 12 is a cross sectional view of the connection 301 between two example relative positioning structures 290 and 294. In this example, the connection 301 is between a female 300 and male 308 coupling, supported by the bodies 302 and 306 respectively, forming a snug fit 314 and 316, with voids 310 and 312. In other embodiments, the engine accesses templates containing different designs of relative positioning structures when the engine adds the positioning structures to the electronic model in operation 282. The connection 301 is shown in more detail in FIGS. 13-15.

The void 310 enables the male coupling 308 to fit within the female coupling 300 even if debris has settled within the female end's cavity or on the end of the male coupling. In some embodiments, the void's 310 space is formed between the top of the truncated cone male coupling 308 and the deepest part of the female coupling 300.

The voids 310 and 312 enable a snug fit between the male coupling 308 and the female coupling 300 even if debris has settled near the opening of the female coupling 300 or on the male coupling 308 close to where the coupling 308 meets the body 306. In some embodiments, the void 312 space is formed near the opening of the female coupling 300 and the body of the male coupling 308.

The two couplings 300 and 308 form a snug fit within the female coupling 314 and where the bodies meet 316. In some embodiments, the lateral surface of the male coupling 308 is flush with the lateral surface of the female coupling 300, forming an interface 314 where the two couplings are, or nearly are, in direct contact. In some embodiments, the surface of the bodies 302 and 306 that is parallel to the x-y-plane form an interface 316 where the two bodies are, or nearly are, in direct contact. In the preferred embodiment, the snug fit ensures that the upper 162 and lower 164 arch dentitions do not change their relative positions during the surgical splint forming (at station 130).

Figure 13:
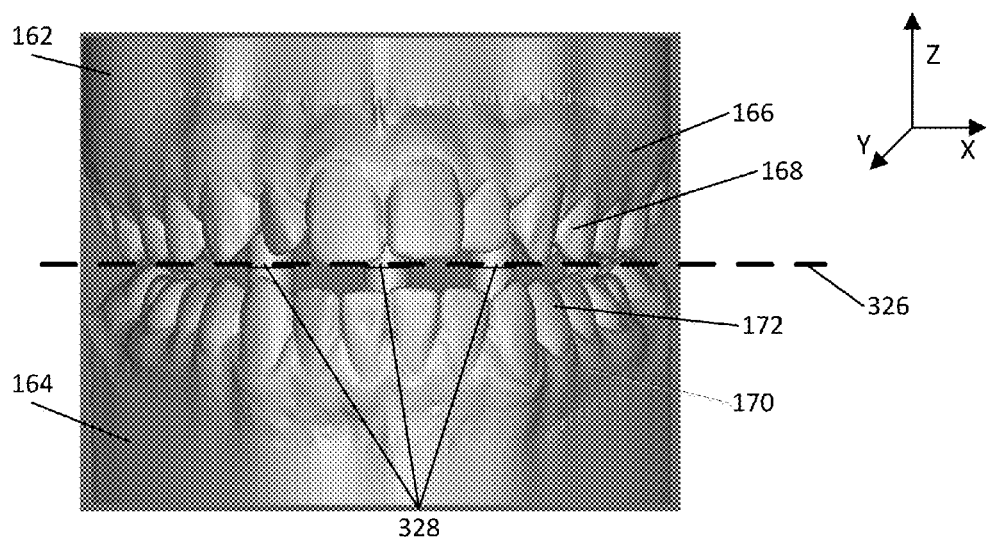
FIG. 13 illustrates a front view of an example corrected arch dentition model with relative positioning structures.
Figure 14:
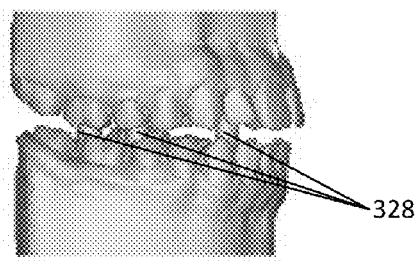
FIG. 14 illustrates a left-side view of an example corrected arch dentition model with relative positioning structures.
Figure 15:
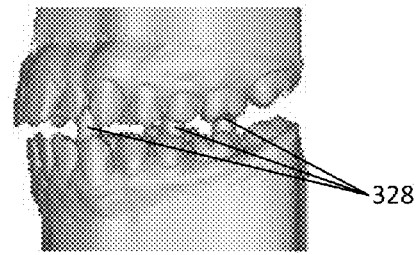
FIG. 15 illustrates a right-side view of an example corrected arch dentition model with relative positioning structures.

FIGS. 13-15 illustrate different views of the corrected arch dentition model 124 with connected relative positioning structures 328. FIG. 13 is a front view illustrating the upper 162 and lower 164 arch dentitions, the maxillary 166 and mandibular 170 gingiva, the upper 168 and lower 172 dentition, the connected relative positioning structures 328, and the midpoint x-y-plane 326 between the upper 162 and lower 164 arch dentitions. FIG. 14 is a left-side view illustrating the connected relative positioning structures 328. FIG. 15 is a right-side view also illustrating the connected relative positioning structures 328.

The connected relative positioning structures 328 hold the upper 162 and lower 164 dentitions in the relative positions defined by the orthodontist O 278. In a preferred embodiment, the upper 290 and lower 294 positioning structures interface 301 at the x-y-plane midpoint 326 between the upper 162 and lower 164 arch dentitions. In other embodiments, the interface 301 is located at positions other than the x-y-plane midpoint.

Figure 18:
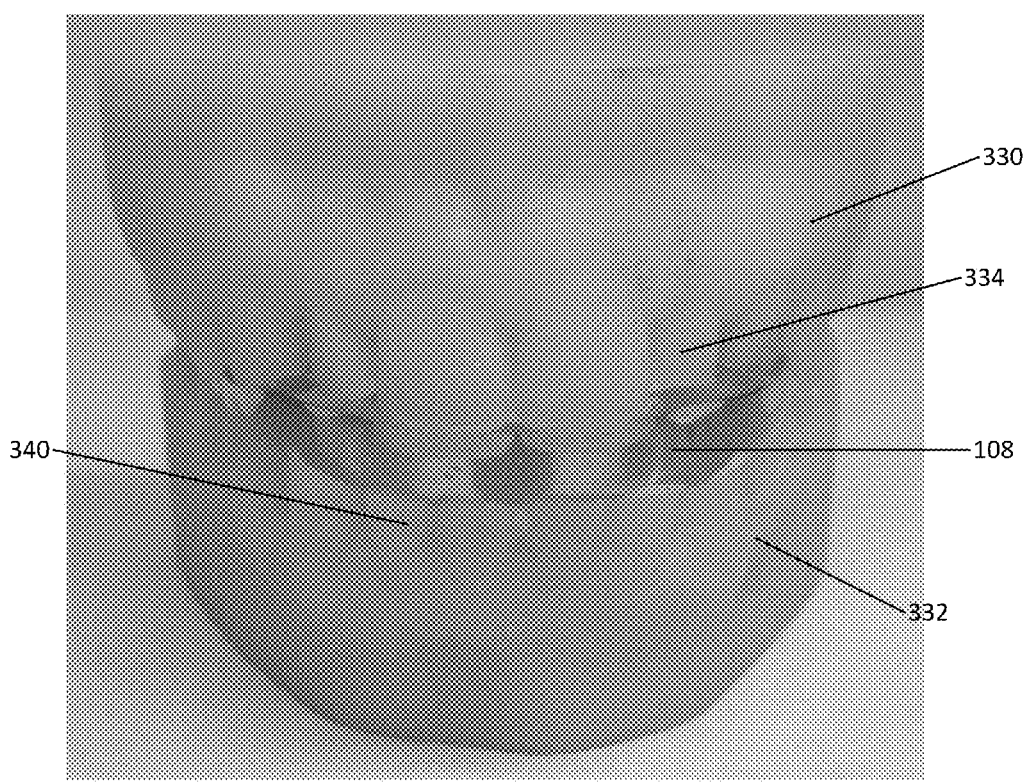
FIG. 18 illustrates a front perspective view of the example physical model of a patient's corrected dentition with a surgical splint.
Figure 19:
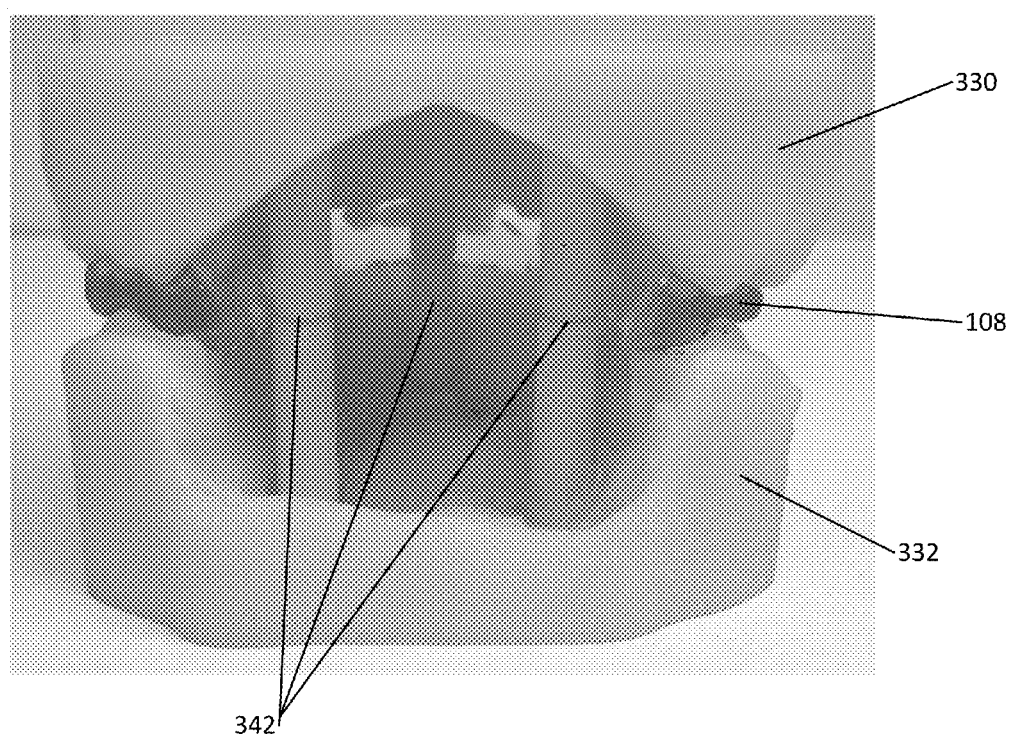
FIG. 19 illustrates a rear perspective view of the example physical model of a patient's corrected dentition with relative positioning structures and with a surgical splint, as shown in FIG. 18.

FIG. 16 is a front perspective view of a physical model 128 of a patient's corrected dentition. In this example, the physical model 128 includes the upper arch dentition 330 and the lower arch dentition 332. Present, but not visible in FIG. 16, are the connected relative positioning structures 342 which can be seen in FIG. 17. Additional exemplary views of the physical model 128 are also shown in FIGS. 17-19.

The upper arch dentition 330 of the physical model 128 of the patient's corrected dentition is a replication of the patient's upper dentition 334 and maxillary gingiva 336. In this embodiment, the physical model's 128 upper dentition 334 contours substantially match the patient's P actual upper dentition contours, so that a surgical splint can be made from the physical model 128 that fits snugly into the patient's dentition. The contours in the splint are shown in more detail in FIG. 20. In some embodiments, the upper arch dentition 330 is separable from the lower arch dentition 332, but the model 128 can be properly aligned and positioned by the connected relative positioning structures 342. The upper arch dentition 330 is also depicted in FIGS. 17-19.

The lower arch dentition 332 of the physical model 128 of the patient's corrected dentition is a replication of the patient's lower dentition 340 and mandibular gingiva 338. In this embodiment, the physical model's 128 lower dentition 340 contours substantially match the patient's P actual lower dentition contours, so that a surgical splint can be made from the physical model 128 that fits snugly into the patient's dentition. The contours in the splint are shown in more detail in FIG. 20. In some embodiments, the lower arch dentition 332 is separable from the upper arch dentition 330, but the model 128 can be properly aligned and positioned by the connected relative positioning structures 342. The lower arch dentition 332 is also depicted in FIGS. 17-19.

The distance D4 between two corresponding points on the upper 330 and lower 332 arch dentitions provides the space needed for the splint to fit during the operation. In one embodiment, the engine received the user's input of the distance D4 in methods 270 and 280, shown in more detail in FIG. 6. In some embodiments, the distance D4 corresponds to the surgical splint material's properties. In some embodiments, the distance D4 in the physical model 128 is maintained by the relative positioning structures 346 depicted in more detail in FIGS. 17 and 19.

FIG. 17 is a rear perspective view of a physical model of a patient's corrected dentition 128. In this example, FIG. 17 shows the upper 330 and lower 332 arch dentitions, and the connected relative positioning structures 342 formed by the positioning structures attached to the upper 344 and lower 346 arch dentitions. FIG. 19 shows a similar view with the surgical splint 108.

The connected relative positioning structures 342 function to hold the upper 330 and lower 332 arch dentitions in the relative positions defined by the orthodontist O. In this example, the interface between the upper 344 and lower 346 relative positioning structures occurs at the midpoint in the z-plane between the upper 330 and lower 332 arch dentitions. In some embodiments, the relative positioning structures 344 and 346 form a releasable coupling, shown in more detail in FIGS. 10-12. In some embodiments, the connected relative positioning structures 342 maintain the distance D4 between corresponding points, as shown in more detail in FIG. 16, to assist surgical splint formation and functionality.

The upper relative positioning structures 344 couple to the lower positioning structures 346 to form the connected relative positioning structures 342. In some embodiments, the upper 344 and lower 346 positioning structures extend from the surface contouring the patient's mouth that is not the dentition or gingiva. In some embodiments, the upper 344 and lower 346 positioning structures project a given distance away from the dentition so as to not interfere with the splint positioning or formation. In this example, the positioning structures 344 and 346 are cylindrical, as electronically depicted in FIGS. 10-11, and couple as depicted in FIG. 12.

FIG. 18 is a front perspective view of the physical model of the patient's corrected dentition 128 with the surgical splint 108. In this example, FIG. 18 shows the upper 330 and lower 332 arch dentitions, the upper 334 and lower 340 dentitions, and the surgical splint 108. A rear perspective view of the same is shown in FIG. 19, and the surgical splint 108 is shown in more detail in FIG. 20.

The surgical splint 108 maintains the relative positioning of the upper 330 and lower 332 arch dentitions as defined by the orthodontist O. Surgical splint formation techniques are described in more detail in FIG. 1, with reference to 130 and 108. In some embodiments, the upper surface of the surgical splint 108 has contours that match the contours of the patient's upper dentition 334. In some embodiments, the contours have a depth in a range from about 0.1 mm to about 3 mm. Other embodiments have other dimensions. Similarly, in some embodiments, the lower surface of the surgical splint 108 has contours that match the contours of the patient's lower dentition 340. In some embodiments, the contours have a depth in a range from about 0.1 mm to about 3 mm. Other embodiments have other dimensions.

FIG. 19 is a rear perspective view of the physical model of the patient's corrected dentition 128 with the surgical splint 108. In this example, FIG. 19 shows the upper 330 and lower 332 arch dentitions, the connected relative positioning structures 342, and the surgical splint 108. The surgical splint 108 is shown in more detail in FIG. 20.

The surgical splint 108 functions to hold the upper 330 and lower 332 arch dentitions in the relative positions as defined by the orthodontist O. In this example, the distance D4 between corresponding points is the same with the surgical splint 108 place between the upper 330 and lower 332 arch dentitions. In some embodiments, the connected relative positioning structures 342 are not in contact with the surgical splint 108.

Figure 20:
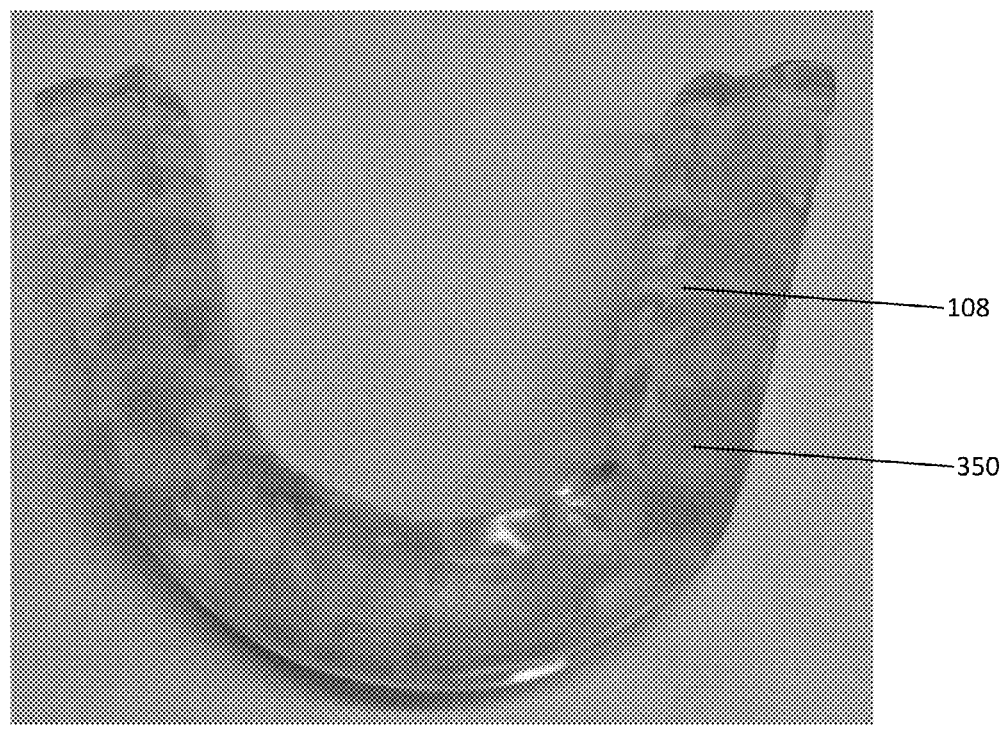
FIG. 20 illustrates a front perspective view of the surgical splint, as shown in FIG. 18.

FIG. 20 is a front perspective view of a surgical splint 108. In this example, FIG. 20 shows the surgical splint 108 with the contours 350 of the patient's upper dentition 334. In this example, the surgical splint also contains contours 350 on the opposing surface which correspond to the contours of the patient's lower dentition 340. Surgical splint formation techniques are described in more detail in FIG. 1, with reference to 130 and 108. In some embodiments, each of the patient's teeth has a corresponding contour 350 in the splint 108. In one embodiment, when the patient's teeth are placed in the splint, the relative positions of the upper 330 and lower 332 arch dentitions correct the diagnosed problem. In some embodiments, the splint 108 contours 350 are of a depth that will hold the upper 330 and lower 332 dentitions in the required relative positions but the splint 108 will also be removable from both the physical model 128 and the patient P.

Figure 21:
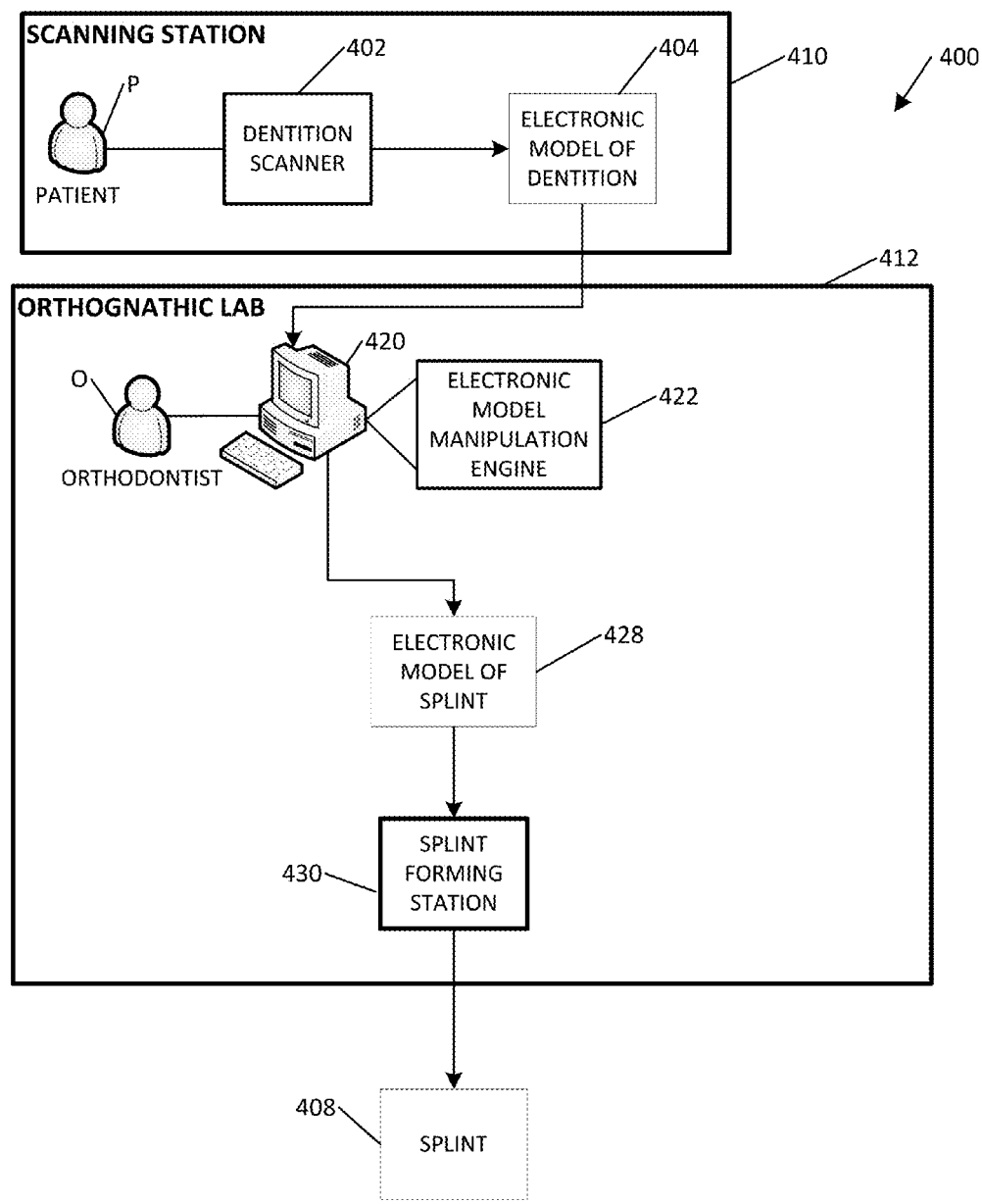
FIG. 21 illustrates a schematic block diagram illustrating an example system for making a splint without first creating a physical corrected arch dentition model with relative positioning structures.

FIG. 21 is a schematic block diagram illustrating an example of a system 400 for making a maxillofacial splint 408 without first creating a physical corrected arch dentition model with relative positioning structures. In this example, the system 400 includes a scanning station 410 and an orthognathic lab 412. The example scanning station 410 includes a dentition scanner 402 that generates an electronic model of a patient's dentition 404. The example orthognathic lab 412 includes a computing device 420, an electronic model manipulation engine 422, an electronic model of a splint 428, and a splint forming station 430. The resulting physical splint 408 can be used for orthognathic surgery or to treat any type of jaw-related disorder, such as sleep apnea or TMD. Also illustrated in FIG. 1 are examples of several people that may be involved with the system 400, including the patient P and orthodontist O.

The scanning station 410 operates to perform a scan of the patient's P dentition, such as using a dentition scanner 402. In some embodiments, the patient P has been identified as having a dental condition in which the relative positioning of the maxillary and mandibular dentitions needs to be adjusted. Several examples of such dental conditions include, but are not limited to, a Class II overjet or Class III negative overjet, temporomandibular joint disorder (TMD), or sleep apnea.

The scanner 402 operates to perform a scan of the patient's dentition. The scanner 402 can be one of several types, for example, including an intraoral scanner, a table top laser scanner, or a computed tomography (CT) scanner. In some embodiments, the scanner is a three-dimensional laser scanner that generates data defining a polygonal mesh forming the electronic model 404 of the dentition. In some embodiments, the scanner 402 first projects points onto the surface, here, the patient's dentition. The reflection of these points off of the patient's dentition enables the scanner to obtain the location of points in a three-dimensional coordinate system (x, y, z). These points are used to create a point cloud corresponding to the contours of the patient's dentition. Next, the scanning system creates a polygonal mesh by using the point cloud to create triangles that approximate the surface contours. Examples of scanners 402 include a 3D scanner, intraoral scanner, 3D intraoral scanner, or 3D dental scanner. The electronic model may be obtained by placing the scanner in the patient's mouth, by scanning a dental impression, or by scanning from outside of the mouth. Several examples of possible scanners 402 include: the TRIOS Intra Oral Digital Scanner, the Lava Chairside Oral Scanner C.O.S., the iTero, the Cerec AC, the Cyrtina IntraOral Scanner, a cone beam CT (CBCT) scanner, and an industrial CT scanner.

The electronic model 404 of the dentition includes, for example, the maxillary and mandibular dentition, and shows the undesired relative positioning of each that needs to be surgically corrected. Examples of such electronic models 404 are illustrated and described in more detail herein with reference to FIGS. 2 and 3.

The orthognathic lab 412 generates a physical splint 408 using the electronic model of a splint 428. The example orthognathic lab 412 includes a computing device 420 including an electronic model manipulation engine 422 and a splint forming station 430.

The computing device 420 operates to generate an electronic model of a splint 428 using the electronic model of dentition 404. An example of the computing device 420 is illustrated and described in more detail herein with reference to FIG. 4. In some embodiments, the computing device 420 includes an electronic model manipulation engine 422. The user, such as an orthodontist O, interacts with the computing device 420 and electronic model manipulation engine to adjust the relative positioning of the maxillary and mandibular dentitions to form a corrected arch dentition model 464 and an electronic model of a splint 428. An arch dentition includes the dentition, gingiva, and contour of a patient's upper or lower jaw. An example of the electronic model manipulation engine 422 is illustrated and described in more detail herein with reference to FIGS. 22-23.

In one embodiment, after the orthodontist O adjusts the relative positioning of the maxillary and mandibular dentitions, the electronic model manipulation engine 422 generates an electronic model of a splint 428. In some embodiments, the electronic model of a splint 428 includes, for example, the impressions of the maxillary and mandibular dentitions after realignment by an orthodontist O and the surrounding support structure. The generation of the electronic model of a splint 428 is illustrated and described in more detail herein with reference to FIGS. 22-25.

In some embodiments, the splint forming station 430 receives the electronic model of the splint 428 via a wired or wireless connection between the computing device 420 and the splint forming station 430. Alternatively, portable storage media, such as, for example, a USB-connected memory drive, is used to transfer the electronic model of a splint 428 to the splint forming station 430.

The splint forming station 430 operates to generate a physical splint 408 for the patient P from the electronic model of a splint 428. In some embodiments the splint forming station 430 includes a rapid fabrication machine. One example of a rapid fabrication machine is a three dimensional printer. Another example of a rapid fabrication machine is a milling device, such as a computer numerically controlled (CNC) milling device. Examples of three-dimensional printers, their operation, and example materials are discussed in more detail above with reference to FIG. 1. In some embodiments the rapid fabrication machine is or includes a deposition device, such as a three dimensional printer, which deposits a material to form the splint 428. In other embodiments the rapid fabrication machine is or includes a milling device, which removes material to form the splint 428. Some embodiments include a deposition device and a milling device.

In some embodiments, when the splint 428 is formed by a rapid fabrication machine, the splint 428 has physical characteristics that show that the splint 428 was formed by a rapid fabrication machine. One example of a physical characteristic is the multi-layered structure of the body, such as when the body is formed by a three-dimensional printer or other deposition device. The deposition device deposits the material in a plurality of rows and layers, which are detectable in the splint 428. Another example of a physical characteristic is the presence of a plurality of grooves on the surface of the splint. The sizes of the grooves correspond with the resolution of the rapid fabrication machine. For example, when a deposition device is used, a finite resolution of the deposition device results in small groves along at least some of the outer surfaces of the splint 428, particularly along rounded or curved edges. When a milling device is used, the finite resolution of the milling device also results in small groves along at least some of the outer surfaces of the splint 428. In addition to the example materials previously described herein, in some embodiments the splint forming station produces bi- or tri-laminar splints. For example, a soft, shock-absorbing layer is used for the points of contact with the patient's P teeth and a harder layer is used for the remainder of the splint. Additional splint-forming materials used in some embodiments include any material approved for use in the mouth, such as, for example, Stratasys™ bio-compatible PolyJet photopolymer and Stratasys™ VeroDent.

In some embodiments, the splint forming station 430 comprises a computer numerically controlled (CNC) milling device. In this embodiment, a block or chunk of one or more materials is placed into a CNC milling device. The CNC milling device receives the electronic model of the splint 428 and accordingly uses the model 428 to produce the splint 408 for use by the patient P.

Figure 22:
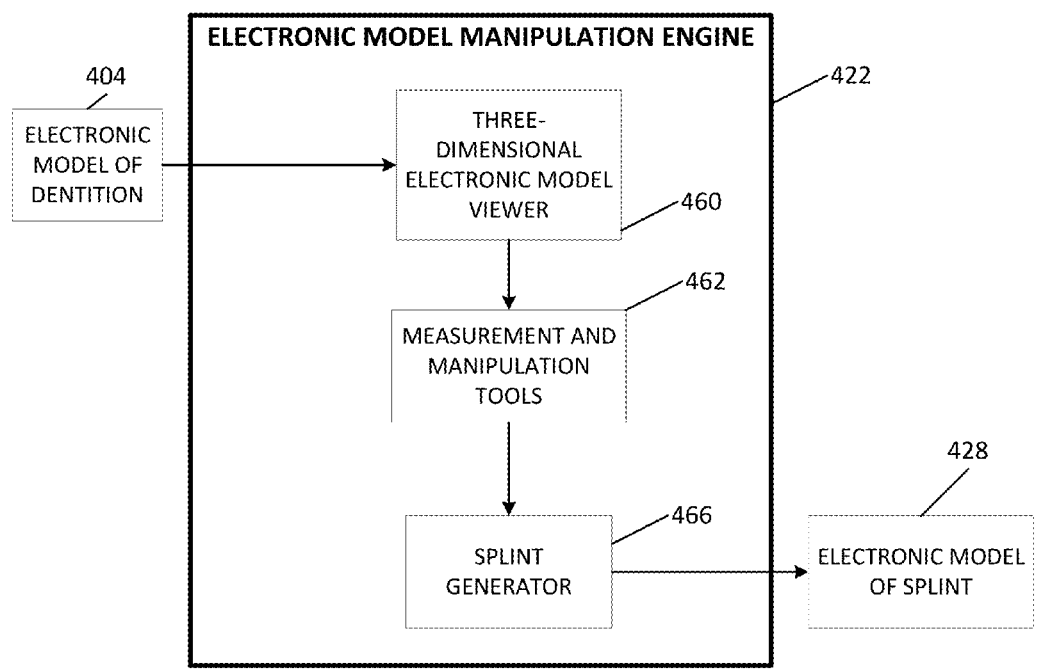
FIG. 22 illustrates a schematic block diagram illustrating an alternative example electronic model manipulation engine.

FIG. 22 is a schematic block diagram illustrating an example embodiment of the electronic model manipulation engine 422. In this example, the model manipulation engine 422 includes a three-dimensional electronic model viewer 460, measurement and manipulation tools 462, and a splint generator 466. Also illustrated in FIG. 22 are the electronic model of dentition 404 and the electronic model of the splint 428.

The three-dimensional electronic model viewer 460 is described in more detail above with reference to FIG. 5 and model viewer 260. Similarly, the measurement and manipulation tools 462 are described in more detail above with reference to FIG. 5 and tools 262, as well as the electronic model of dentition 404 with reference to FIG. 5 and model 104.

The splint generator 466 operates to create the electronic model of the splint 428. In one embodiment, after the orthodontist O repositions the relative alignment of the upper 162 and lower 164 arch models using the measurement and manipulation tools 462, the splint generator receives the arch dentition model. The splint generator is described in more detail herein with reference to FIG. 23.

Figure 23:
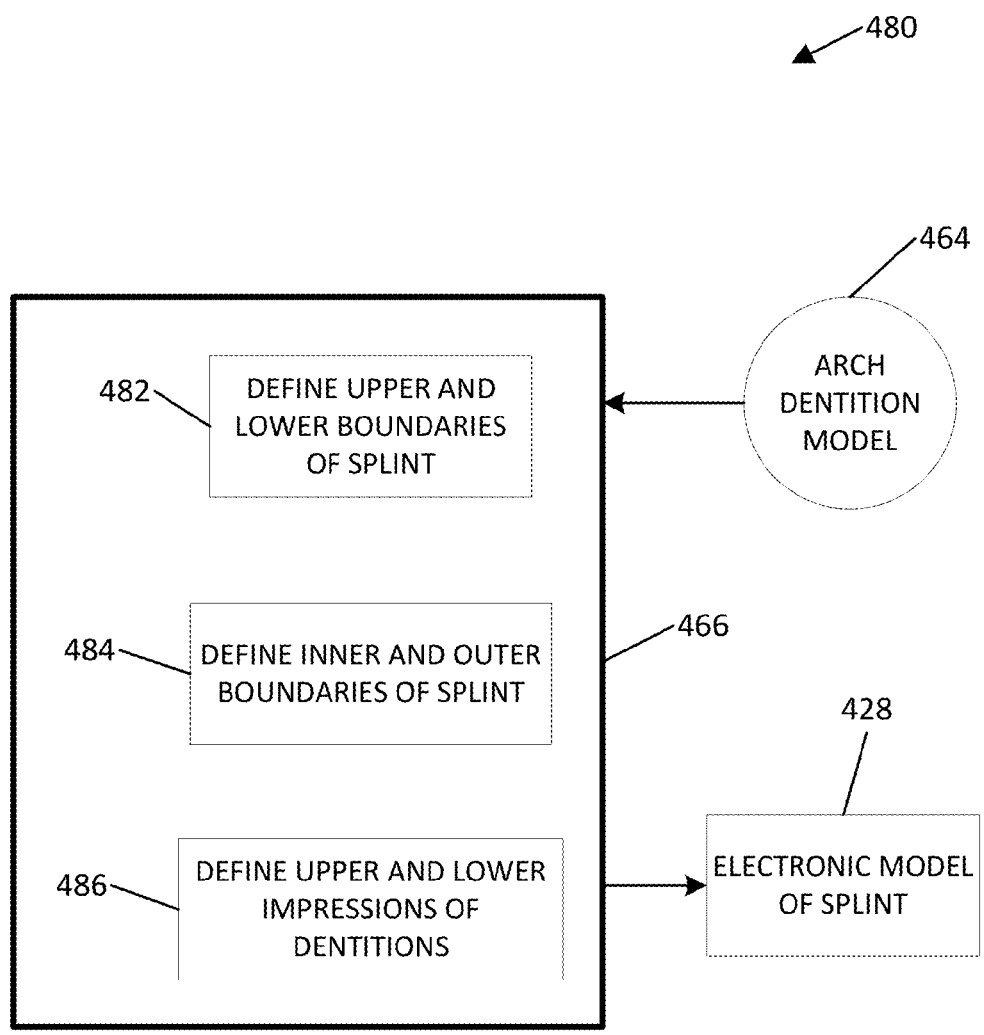
FIG. 23 illustrates a schematic block diagram illustrating an example generation of an electronic model of a splint.

FIG. 23 is a flow chart illustrating an example method 480 of generating an electronic model of a splint 428. In this example, the method 480 includes the splint generator 466 receiving the arch dentition model 464, defining upper and lower boundaries 482 of the splint 428, defining inner and outer boundaries 484 of the splint, defining upper and lower impressions of the dentitions 486, and generating an electronic model of a splint 428. Operations 482, 484, and 486 can be performed in any order.

Figure 24:
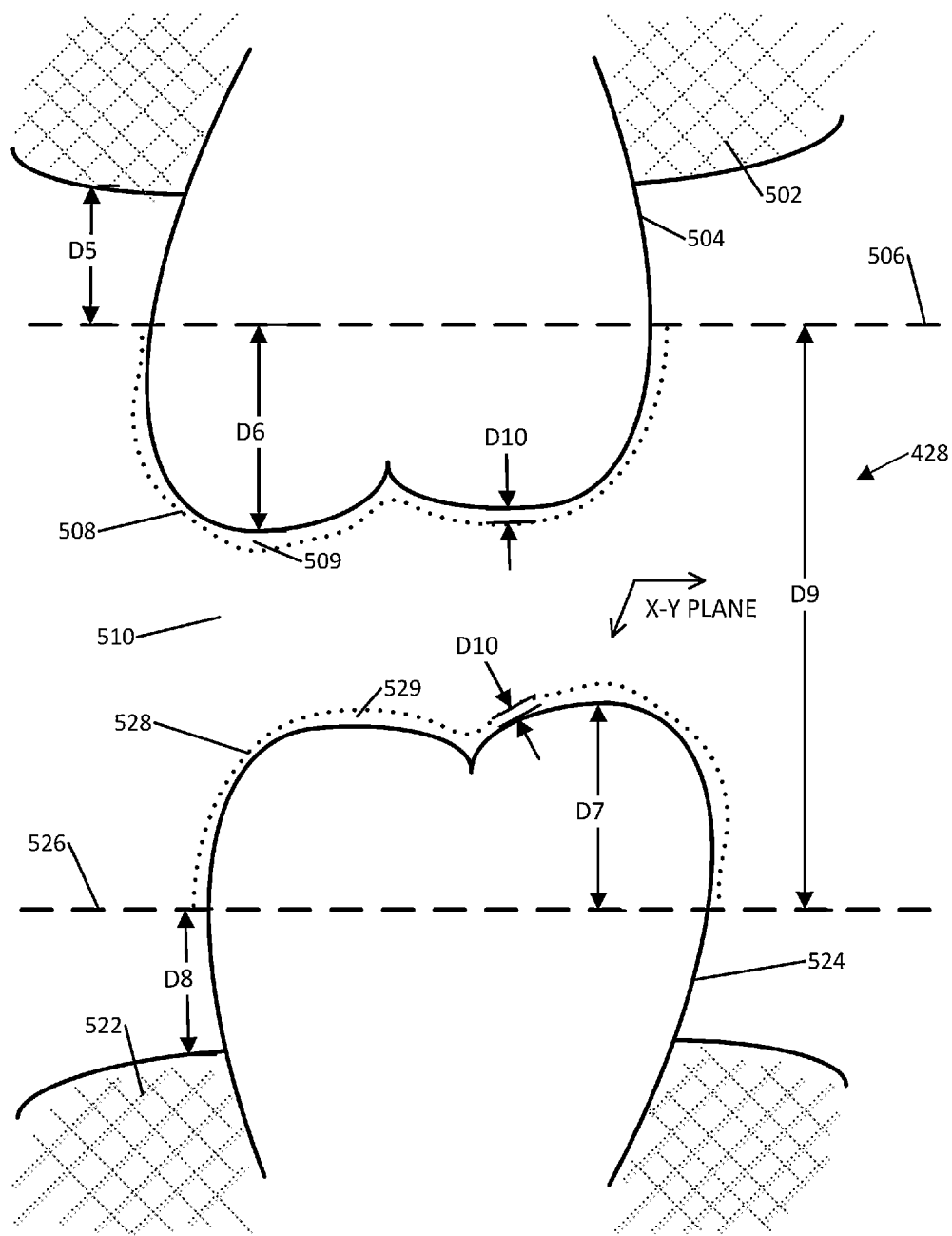
FIG. 24 illustrates a two-dimensional side view of an example cross-section of a splint and an upper and a lower tooth.

Operation 482 is performed to define the upper and lower boundaries of the splint 428. With reference to FIG. 24, the splint 428 has an upper boundary 506, a lower boundary 526, and a thickness D9. The upper boundary 506 of the splint 428 and the lower boundary 526 of the splint 428 are separated by distance D9.

In one embodiment, the upper boundary 506 of the splint 428 is the x-y plane surface closest to the upper dentition and the lower boundary 526 is the x-y plane surface closet to the lower dentition. In one embodiment, the splint generator 466 sets the upper boundary 506 a distance D5 from the maxillary gingiva 502. Similarly, in one embodiment, the splint generator 466 sets the lower boundary 526 a distance D8 from the mandibular gingiva 522. The orthodontist O sets, in this example, the specified distances D5 and D8, which are not necessarily the same value.

In some embodiments, the upper 506 and lower 526 boundaries are the same throughout the splint 428 such that the splint 428 has the same thickness D9 throughout. In other embodiments, the resulting splint 428 is a compilation of the cross sections for each pair of corresponding teeth and has a variable thickness D9.

In another embodiment, the splint generator 466 identifies the tooth in the upper arch dentition that extends the least in the z-plane (normal to the maxilla) from the maxillary gingiva 502 and then sets the upper boundary 506 accordingly. For example, the splint generator 466 identifies a distance D6, for example, 3 mm, between the upper boundary 506 and the furthest extension of the tooth 504 from the maxillary gingiva 502. The splint generator 466 then uses that as the upper boundary 506 of the splint 428.

In that embodiment, the splint generator 466 also identifies the tooth in the lower arch dentition that extends the least in the z-plane (normal to the mandible) from the mandibular gingiva 522 and then sets the lower boundary 526 accordingly. For example, the splint generator 466 identifies a distance D7, for example, 3 mm, between the lower boundary 526 and the furthest extension of the tooth from the mandibular gingiva 522. The splint generator 466 then uses that as the lower boundary 526 of the splint 428. This embodiment advantageously ensures that the splint extends in the z-plane sufficiently to such that every tooth in both dentitions has a corresponding impression in the splint 428.

Figure 25:
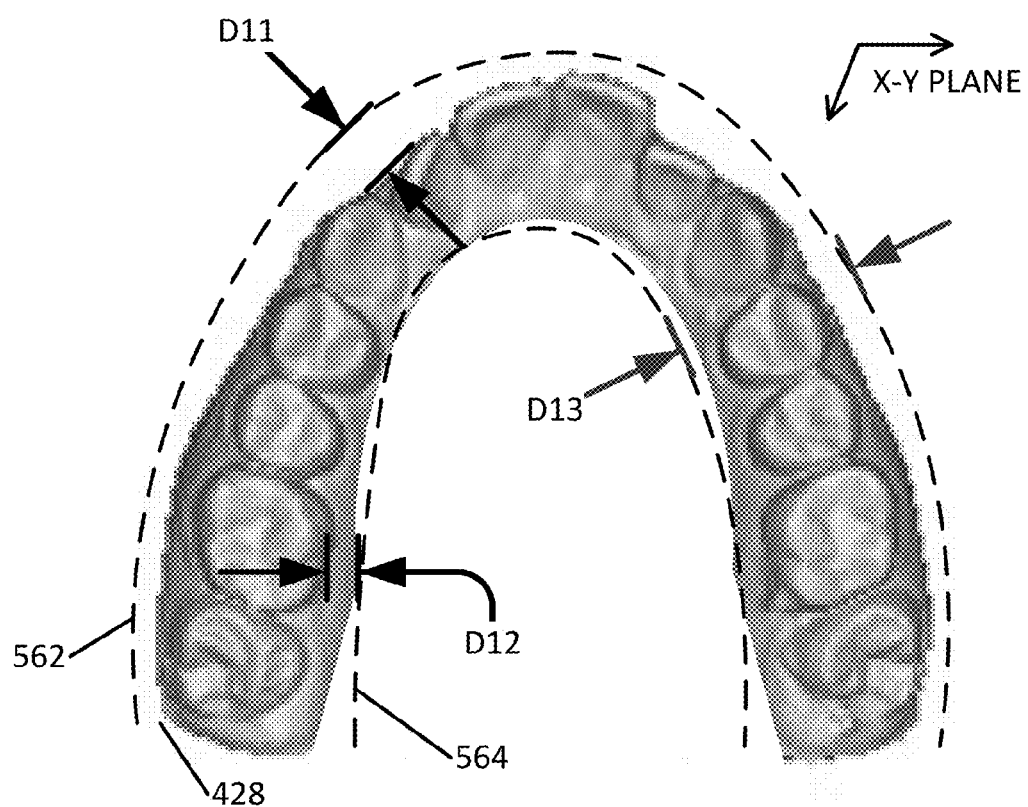
FIG. 25 illustrates a top view of an example upper arch dentition with an example splint's inner and outer boundaries.

Operation 484 is performed to define the inner and outer boundaries of the splint 428. With reference to FIG. 25, the splint 428 has an inner boundary 564, an outer boundary 562, and a width D13. In one embodiment, the inner 564 and outer 562 boundaries are the same for both the upper and lower dentitions. In another embodiment, the inner 564 and outer 562 boundaries are different for the upper and lower dentitions.

In one example embodiment, the splint generator 466 sets the outer boundary 562 a given distance D11 normal to the surface of each tooth. For example, the splint generator 466 sets the outer boundary 562 by calculating the locations of points that are a distance D11 away from the outer surface of each tooth, and the generator 466 uses that set of points to identify the position of an outer boundary 562. In some embodiments the distance D11 is in a range from about 0.01 mm to about 5 mm. In this embodiment, the splint generator 466 sets the inner boundary 564 a given distance D12 normal to the surface of each tooth in a similar fashion by calculating points normal from the inner surface of each tooth.

Operation 486 is performed to define the upper and lower impressions of the dentitions in the splint 428. In one embodiment, as described above with reference to FIG. 21, the dentition scanner 402 has already mapped the contours of each tooth in the electronic model of dentition 404. With reference to FIG. 24, operation 486 accesses those measurements and uses them to create a corresponding impression 508 or 528 (alternatively referred to as cavity, negative impression, or profile) in the splint 428.

In one embodiment, for the upper dentition, the splint generator 466 applies the three-dimensional measurements of the tooth 504, adds a gap buffer of distance D10 and essentially carves out a negative space in the splint 428 for the tooth 504. This results in a tooth impression 508 in the splint 428.

The distance D10 may be set by the orthodontist at, for example, 0.1 mm, and is applied normal to the surface of the tooth 504. In that embodiment, then, there will be a gap buffer 509 to allow small movements of the tooth 504. Additionally, the gap buffer 509 assists the patient P or orthodontist O in removing the splint 408 from the patient's mouth by providing a small amount of space in the tooth impression 528 for the teeth to move.

In other embodiments, the distance D10 is variable, for example, the distance is smallest at the tip of the tooth and increases in the z-plane direction toward the maxillary gingiva 502. The splint generator 466 repeats this process for each tooth and creates a unique impression for each tooth in the upper dentition.

In one embodiment, for the lower dentition, the splint generator 466 applies the three-dimensional measurements of the tooth 524, adds a gap buffer of distance D10 and essentially carves out a negative space in the splint 428 for the tooth 524. This results in a tooth impression 528 in the splint 428.

The distance D10 may be set by the orthodontist at, for example, 0.1 mm, and is applied normal to the surface of the tooth 524. In that embodiment, then, there will be a gap buffer 529 to allow small movements of the tooth. Additionally, the gap buffer 529 assists the patient P or orthodontist O in removing the splint 408 from the patient's mouth by providing a small amount of space in the tooth impression 528 for the teeth to move.

In other embodiments, the distance D10 is variable, for example, the distance is smallest at the tip of the tooth and increases in the z-plane direction toward the mandibular gingiva 522. The splint generator 466 repeats this process for each tooth and creates a unique impression for each tooth in the lower dentition.

In one embodiment, the splint generator 466 defines the splint as the three dimensional space 510 bounded by the upper 506, lower 526, outer 562, and inner 564 boundaries and the upper 508 and lower 528 negative impressions of each tooth. In some embodiments, the splint generator 466 fills that space 510 with the material the three dimensional printer will use to form the splint 408. In other embodiments, the splint generator 466 fills the space with more than one type of material, such as a shock absorbing material in and near the teeth impressions 508 and 528, and a harder material near the inner 564 and outer 562 boundaries.

In some embodiments, the splint generator 466 models the movement of the mandible before finalizing the electronic model of the splint 428. In this example, the splint generator 466 verifies that the gap buffer 509 and 529 is small enough to hold the teeth in the splint 408 yet also large enough to enable small movements of the jaw and assist the patient P or orthodontist O in removing the splint from the patient's mouth.

FIG. 24 is a two-dimensional side view of an example cross-section of a splint and an upper and a lower tooth. The illustrated example shows a maxillary 502 and mandibular 522 gingiva and an upper 504 and lower 524 tooth. The cross section of the splint 428 is shown, with an upper boundary 506 a distance D5 from the maxillary gingiva 502 and a distance D6 from the furthest point in the z-plane from the maxillary gingiva 502, and a lower boundary 526 a distance D8 from the mandibular gingiva 522 and a distance D7 from the furthest point in the z-plane from the mandibular gingiva 522. Tooth impressions 508 and 528 in the space 210 of the splint are also shown, with gap buffers 509 and 529 a distance D10 from the surface of the teeth 504 and 524. The upper and lower boundaries are separated by distance D9. Each aspect of FIG. 24 is discussed in more detail above with reference to FIGS. 22-23.

FIG. 25 is a top view of an example upper arch dentition with a splint's inner and outer boundaries demarcated. The illustrated example shows an inner 564 and outer 562 splint 428 boundary in the x-y plane. The example also shows that the inner boundary 564 is a given distance D12 normal from the inner surface of the teeth, and the outer boundary 562 is a given distance D11 normal from the outer surface of the teeth. The splint 428 has a width D13, which is the distance between the inner 564 and outer 562 boundaries. Similar to the upper 506 and lower 526 boundaries, the width of the splint D13 is constant, or in other examples, the width D13 changes for each tooth. Each aspect of FIG. 25 is discussed in more detail above with reference to FIGS. 22-23.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A non-transitory computer readable storage device storing data instructions thereon, the data instructions being executable by a processing device to cause the processing device to:
   obtain a three-dimensional model of a patient's dentition for use in generating a three-dimensional electronic model of a splint for the patient, wherein the three-dimensional model of the patient's dentition includes a three-dimensional upper dentition model and a three-dimensional lower dentition model;
   obtain a desired alignment of the upper dentition model and the lower dentition model, relative to one another, from a user;
   generate the three-dimensional electronic model of the splint for the patient by causing the processing device to:
   identify a shortest upper tooth in the upper dentition model that extends a smallest distance from the patient's maxillary gingiva in a plane normal to the patient's maxilla, compared to any other teeth in the upper dentition model;
   define an upper boundary of the three-dimensional electronic model of the splint as a first preset distance from a furthest extension of the identified shortest upper tooth toward the maxillary gingiva;

identify a shortest lower tooth in the lower dentition model that extends a smallest distance from the patient's mandibular gingiva in a plane normal to the patient's mandible, compared to any other teeth in the lower dentition model;

define a lower boundary of the three-dimensional electronic model of the splint as a second preset distance from a furthest extension of the identified shortest lower tooth toward the mandibular gingiva;

define an arch-shaped first inner boundary for an upper portion of the three-dimensional electronic model of the splint by calculating locations of inner points that are a third preset distance away from an inner surface of each of the patient's teeth in the upper dentition model and identifying a position of the first inner boundary based on the calculated locations of the inner points;

define an arch-shaped first outer boundary for the upper portion of the electronic model of the splint by calculating locations of outer points that are a fourth preset distance away from an outer surface of each of the patient's teeth in the upper dentition model and identifying a position of the first outer boundary based on the calculated locations of the outer points;

define an arch-shaped second inner boundary for a lower portion of the three-dimensional electronic model of the splint by calculating locations of inner points that are the third preset distance away from an inner surface of each of the patient's teeth in the lower dentition model and identifying a position of the second inner boundary based on the calculated locations of the inner points;

define an arch-shaped second outer boundary for the lower portion of the electronic model of the splint by calculating locations of outer points that are the fourth preset distance away from an outer surface of each of the patient's teeth in the lower dentition model and identifying a position of the second outer boundary based on the calculated locations of the outer points; and generate the three-dimensional electronic model of the splint, using the upper boundary, the lower boundary, the first inner boundary, the first outer boundary, the second inner boundary, the second outer boundary and the desired alignment of the upper dentition model and the lower dentition model, relative to one another;

modify the three-dimensional electronic model of the splint by causing the processing device to:

define an upper impression of an upper dentition in an upper surface of the three-dimensional electronic model of the splint by adding a first gap buffer to three-dimensional measurements of each of the patient's upper teeth and carving out a negative space in the upper surface of the three-dimensional electronic model of the splint corresponding to each of the patient's upper teeth with the added first gap buffer; and define a lower impression of a lower dentition in a lower surface of the three-dimensional electronic model of the splint by adding a second gap buffer to three-dimensional measurements of each of the patient's lower teeth and carving out a negative space in the lower surface of the three-dimensional electronic model of the splint corresponding to each of the patient's lower teeth with the added second gap buffer;

define the three-dimensional electronic model of the splint as a three-dimensional space bounded by the upper boundary, the lower boundary, the first inner boundary, the first outer boundary, the second inner boundary, the second outer boundary, the impression of the upper dentition and the impression of the lower dentition;

store the three-dimensional electronic model of the splint in a computer readable storage device; and control a splint generator to produce the splint in a physical form using the stored three-dimensional electronic model of the splint.

2. The non-transitory computer readable storage device of claim 1, wherein a distance of the first gap buffer is the same as a distance of the second gap buffer, and wherein the distance of the first and second gap buffers are set by an orthodontist.

3. The non-transitory computer readable storage device of claim 2, wherein the distance of the first and second gap buffers is 0.1 millimeters.

4. The non-transitory computer readable storage device of claim 1, wherein a second processing device controls the splint generator to produce the splint.

5. The non-transitory computer readable storage device of claim 1, wherein a second processing device generates the impression of the upper dentition and the impression of the lower dentition.

6. The non-transitory computer readable storage device of claim 1, wherein the first preset distance and the second preset distance are both 3 millimeters.

7. The non-transitory computer readable storage device of claim 1, wherein the third preset distance and the fourth preset distance are both between 0.01 millimeters and 5 millimeters.

* * * * *